(12) United States Patent
Nakashima et al.

(10) Patent No.: US 11,085,916 B2
(45) Date of Patent: Aug. 10, 2021

(54) METHOD FOR OBSERVING DYNAMICS OF SWEAT GLANDS

(71) Applicants: MANDOM CORPORATION, Osaka (JP); OSAKA UNIVERSITY, Suita (JP)

(72) Inventors: Kie Nakashima, Suita (JP); Ryuichiro Kurata, Osaka (JP); Fumitaka Fujita, Osaka (JP); Kiyotoshi Sekiguchi, Suita (JP); Atsushi Tanemura, Suita (JP); Hiroyuki Murota, Suita (JP); Ichiro Katayama, Suita (JP)

(73) Assignees: MANDOM CORPORATION, Osaka (JP); OSAKA UNIVERSITY, Osaka (JP)

( * ) Notice: Subject to any disclaimer, the term of this patent is extended or adjusted under 35 U.S.C. 154(b) by 165 days.

(21) Appl. No.: 16/085,755

(22) PCT Filed: Jul. 18, 2017

(86) PCT No.: PCT/JP2017/026001
§ 371 (c)(1),
(2) Date: Sep. 17, 2018

(87) PCT Pub. No.: WO2018/016501
PCT Pub. Date: Jan. 25, 2018

(65) Prior Publication Data
US 2019/0049429 A1 Feb. 14, 2019

(30) Foreign Application Priority Data
Jul. 19, 2016 (JP) .............................. JP2016-141740

(51) Int. Cl.
| G01N 33/50 | (2006.01) |
| A61B 5/00 | (2006.01) |
| A61K 38/18 | (2006.01) |

(52) U.S. Cl.
CPC .......... *G01N 33/50* (2013.01); *A61B 5/0071* (2013.01); *A61B 5/4266* (2013.01); *G01N 33/5088* (2013.01); *A61K 38/18* (2013.01)

(58) Field of Classification Search
CPC .............. G01N 33/50; G01N 33/5005; G01N 33/5008; G01N 33/5032; G01N 33/521; G01N 33/523; G01N 33/525
See application file for complete search history.

(56) References Cited

U.S. PATENT DOCUMENTS

| 2002/0168763 A1* | 11/2002 | Yan ........................... A61P 1/04 435/325 |
| 2009/0221441 A1 | 9/2009 | Lee et al. |
| 2010/0184213 A1 | 7/2010 | Burry et al. |
| 2016/0075995 A1 | 3/2016 | Kobielak |

FOREIGN PATENT DOCUMENTS

| JP | 2009-513160 A | 4/2009 |
| JP | 2010-522545 A | 7/2010 |
| JP | 2014-66661 A | 4/2014 |
| JP | 2015-31549 A | 2/2015 |

OTHER PUBLICATIONS

Gao et al (Isolation, culture and phenotypic characterization of human sweat gland epithelial cells, International Journal of Molecular Medicine 34, 997-1003, 2014) (Year: 2014).*
Of Tao etal (Isolation, culture, and verification of human sweat gland epithelial cells, Cytotechnology, 2010, 62:489-495) (Year: 2010).*
Lee et al (Biochemical and Ultrastructural Studies of Human Eccrine Sweat Glands Isolated By Shearing and Maintained for Seven Days; Journal of Cellular Science, 72, 259-274, 1984) (Year: 1984).*
Of Lee et al (Biochemical and Ultrastructural Studies of Human Eccrine Sweat Glands Isolated By Shearing and Maintained for Seven Days; Journal of Cellular Science, 72, 259-274, 1984) (Year: 1984).*
Moll et al., "Expression of keratin 5 as a distinctive feature of epithelial and biphasic mesotheliomas", An immunohistochemical study using monoclonal antibody AE14, Virchows Archiv B Cell Pathology Including Molecular Pathology, (1989), vol. 58, pp. 129-145. Cited in Specification. (17 pages).
Kurata et al., "Isolation and Characterization of Sweat Gland Myoepithelial Cells from Human Skin", Cell Structure and Function 39, (2014), pp. 101-112. Cited in ISR. (12 pages).
Gao et al., "Isolation, culture and phenotypic characterization of human sweat gland epithelial cells", International Journal of Molecular Medicine 34, (2014), pp. 997-1003. Cited in ISR. (7 pages).
Brayden et al., "Cultured Human Sweat Gland Epithelia: Isolation of Glands Using Neutral Red", Pharmaceutical Research, (1995), vol. 12, pp. 171-175. Cited in ISR. (5 pages).
International Search Report dated Sep. 19, 2017, issued in counterpart International Application No. PCT/JP2017/026001 (2 pages).

* cited by examiner

*Primary Examiner* — Micah Paul Young
(74) *Attorney, Agent, or Firm* — Westerman, Hattori, Daniels & Adrian, LLP

(57) ABSTRACT

A method for observing the dynamics of sweat glands and a method for evaluating a substance of interest, which are useful for development of a preparation for external application, such as a cosmetic. In each of the methods, an observation sample is used, which is prepared by staining all sweat glands, which are isolated alive, with a staining reagent, and then holding the all sweat glands on a support using at least one material selected from the group consisting of collagen, agarose, basement membrane matrix, poly-D-lysine and a membrane.

10 Claims, 24 Drawing Sheets

[Fig. 1]
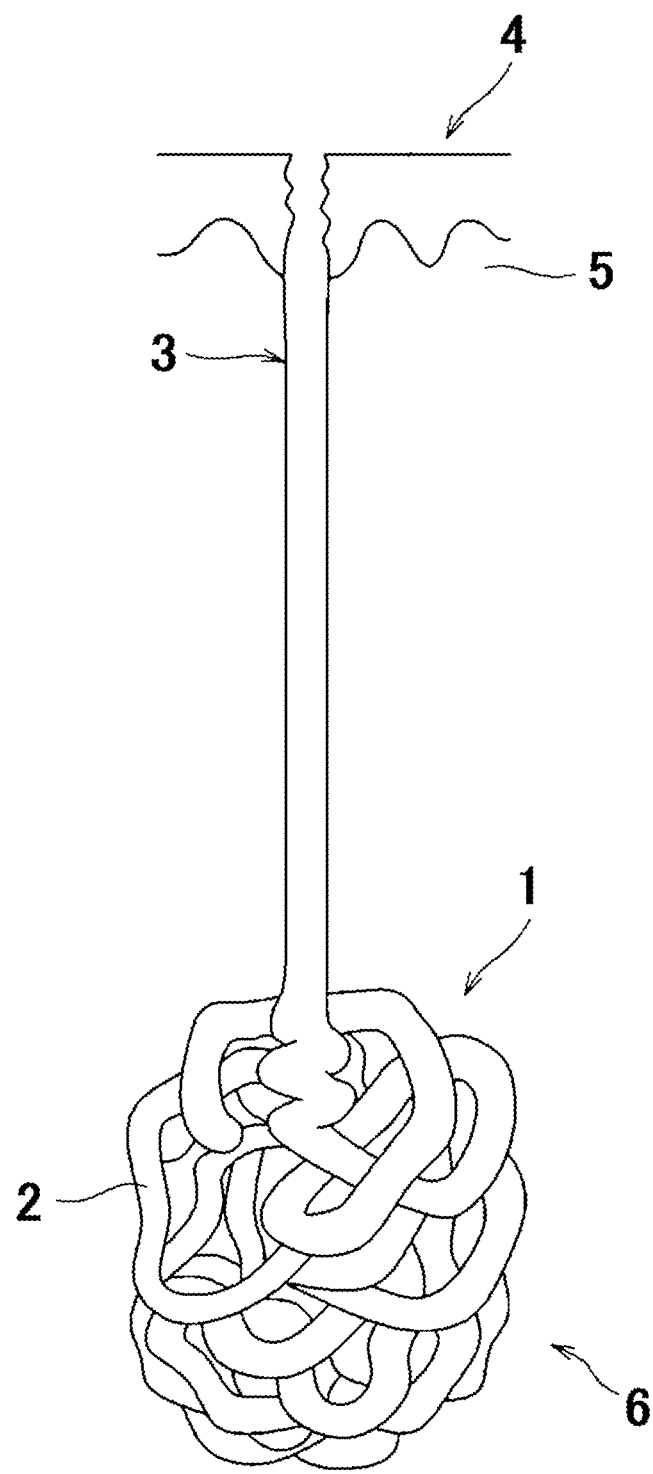

[Fig. 2]
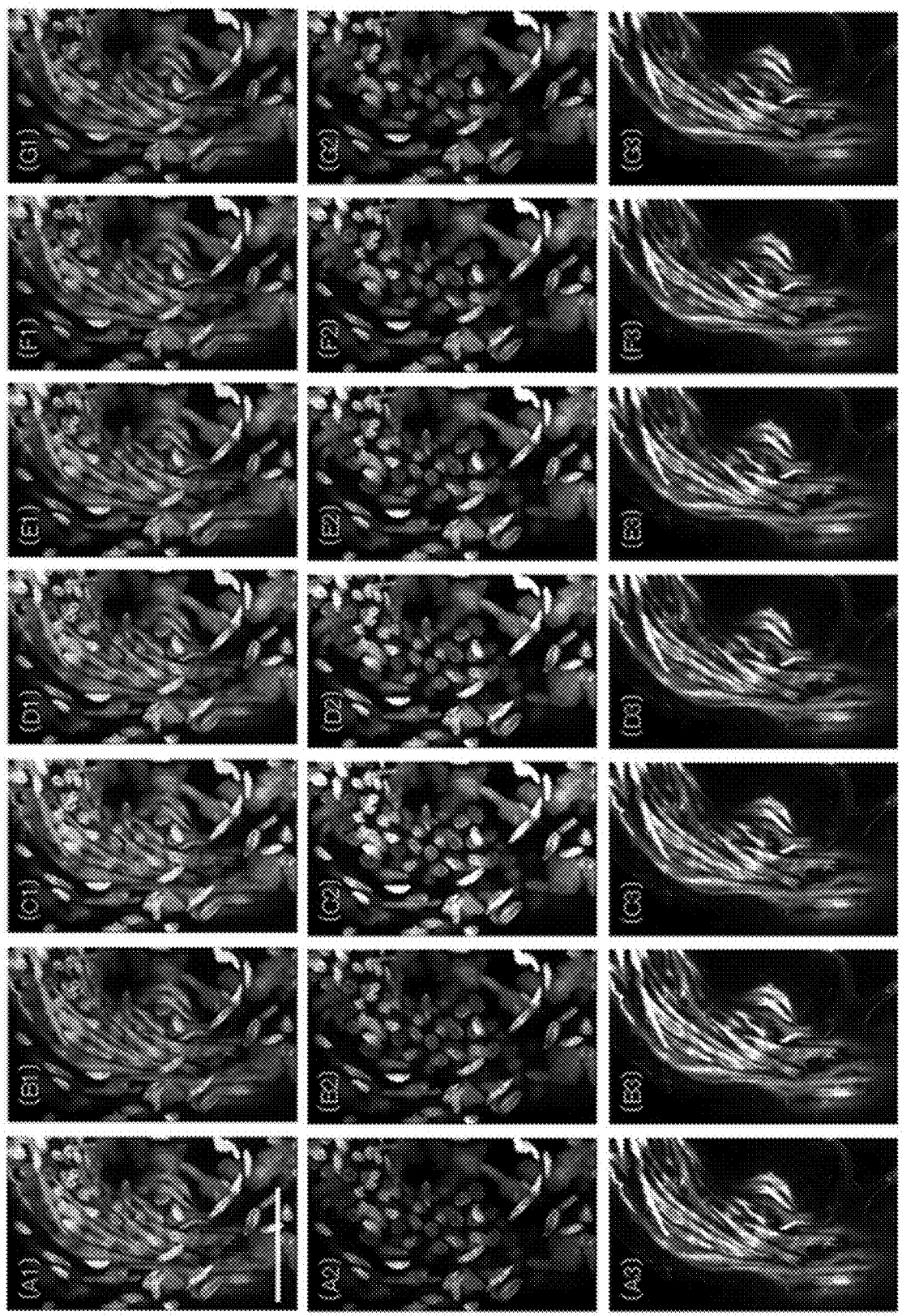

[Fig. 3]
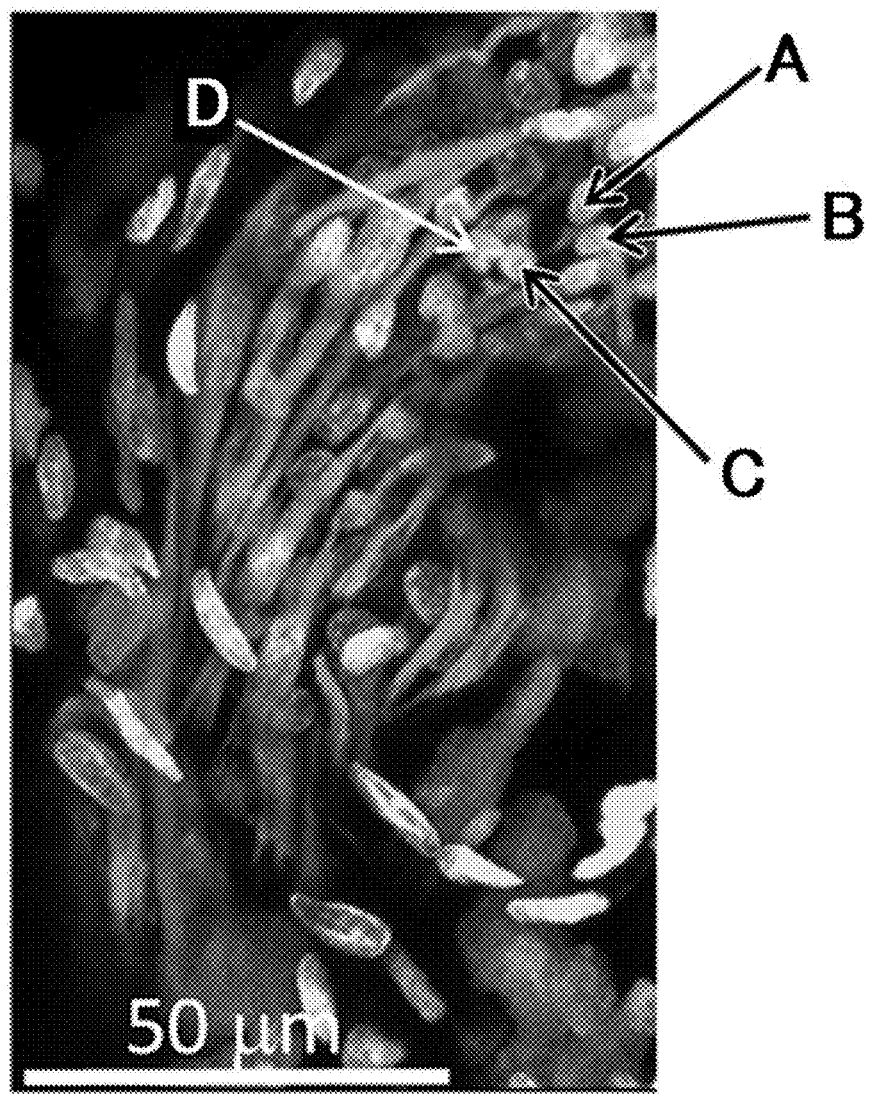

[Fig. 4]
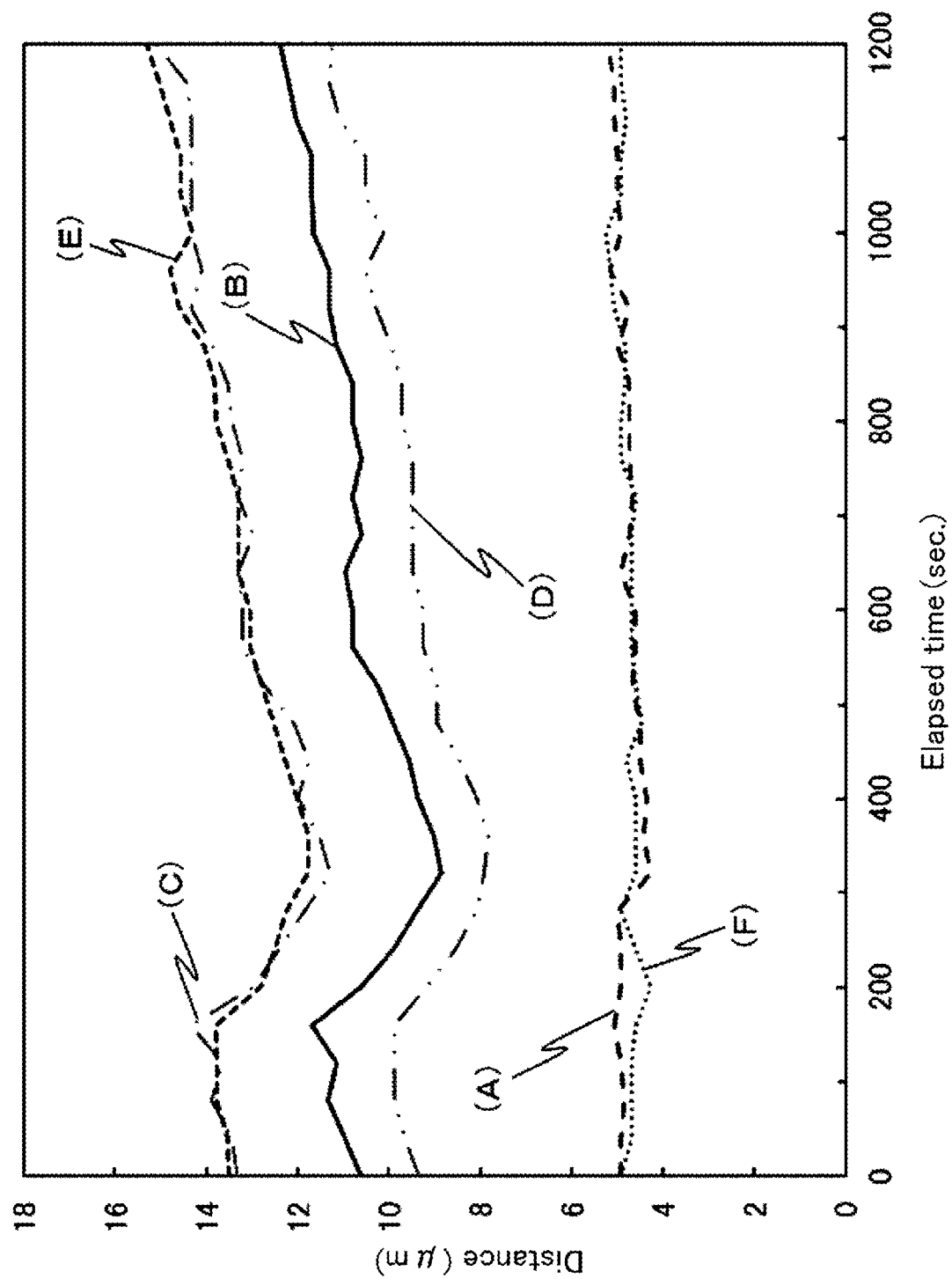

[Fig. 5]
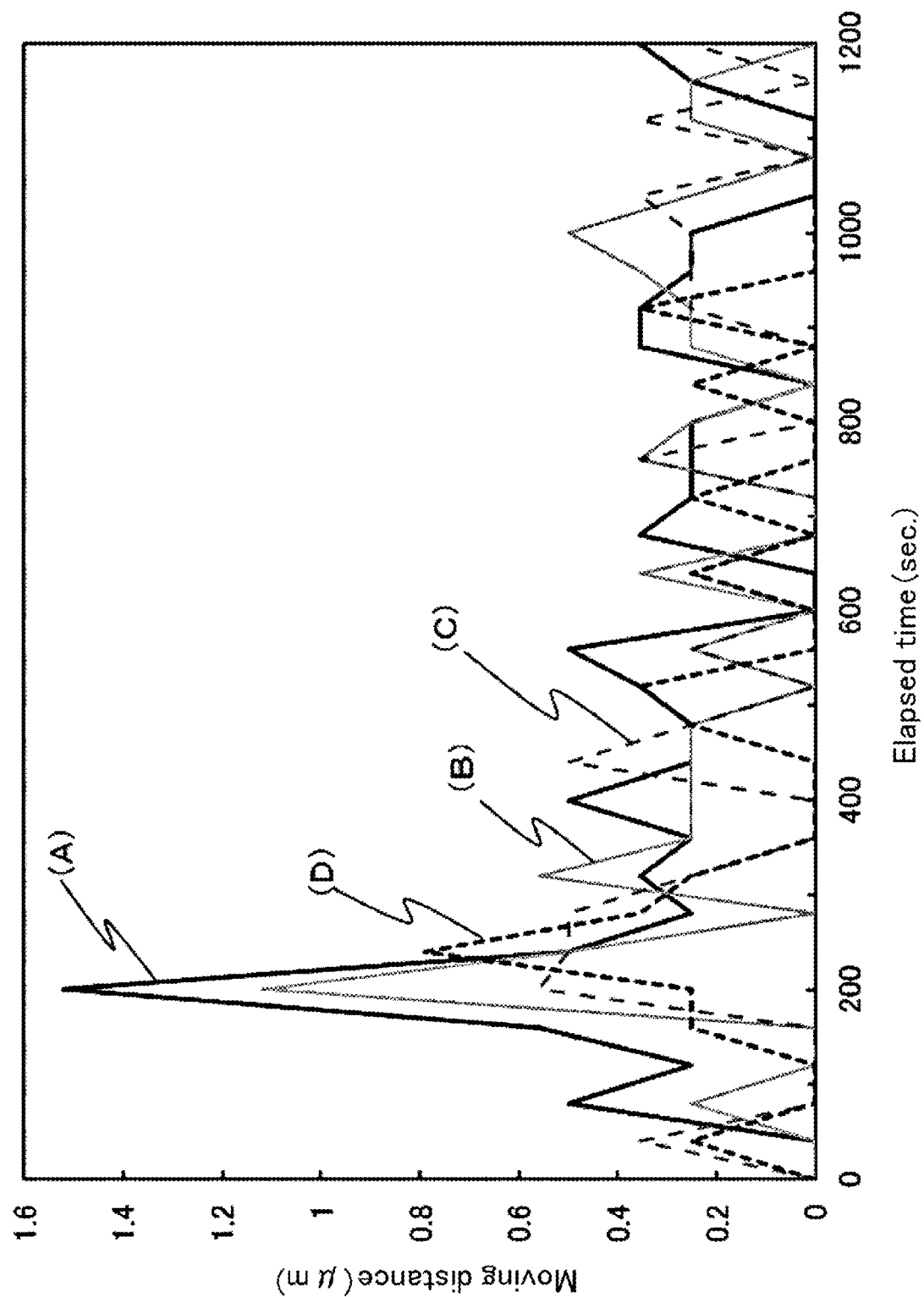

[Fig. 6]
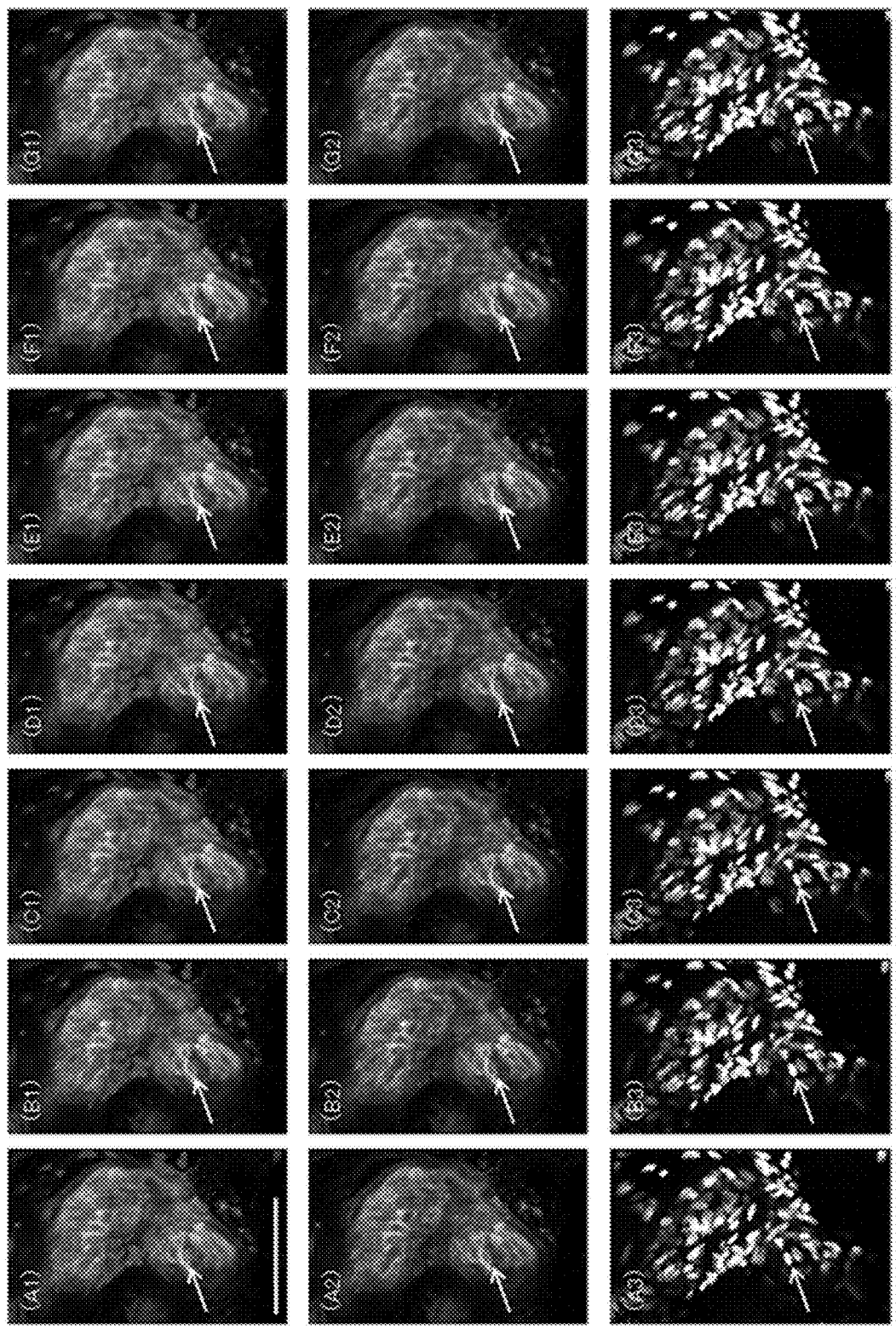

[Fig. 7]
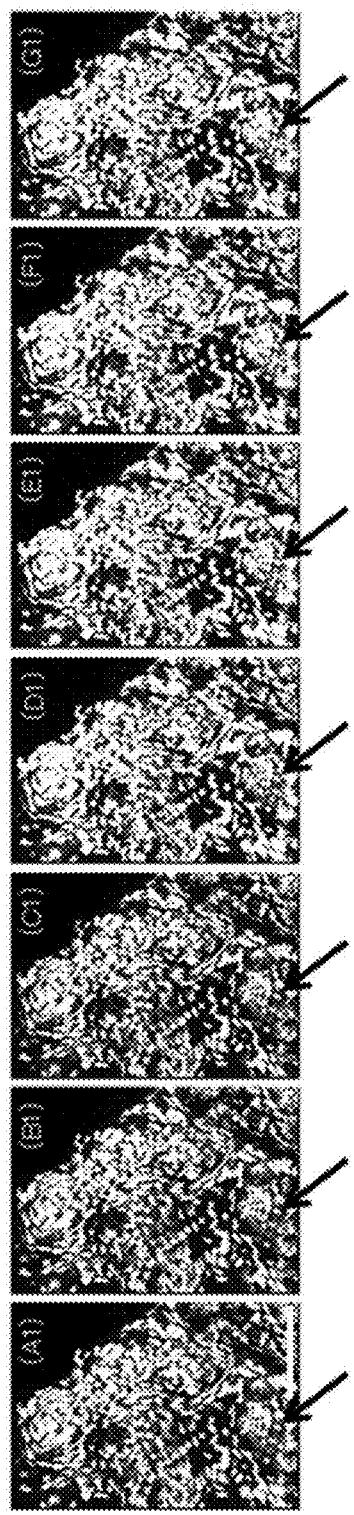

[Fig. 8]
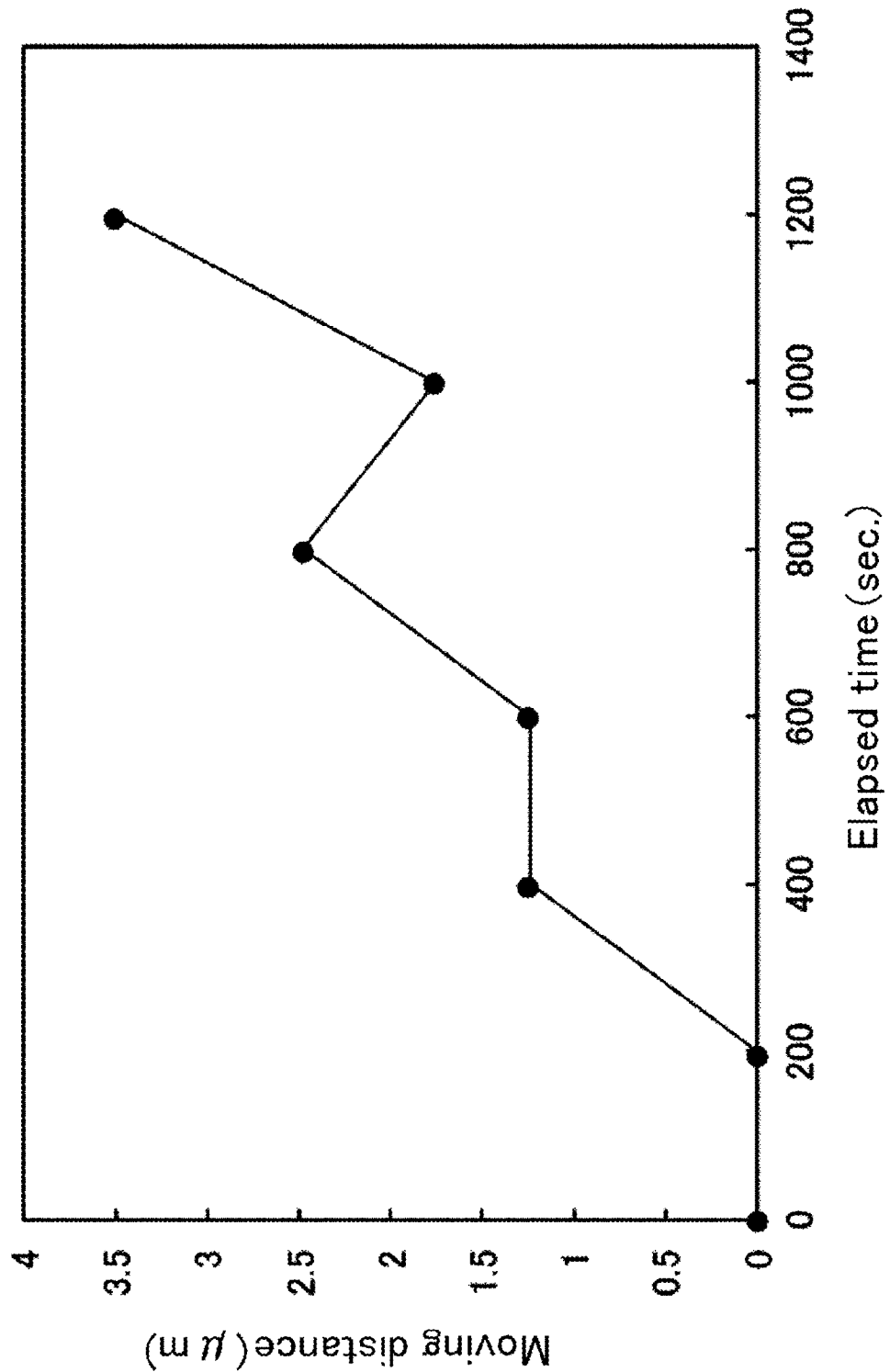

[Fig. 9]
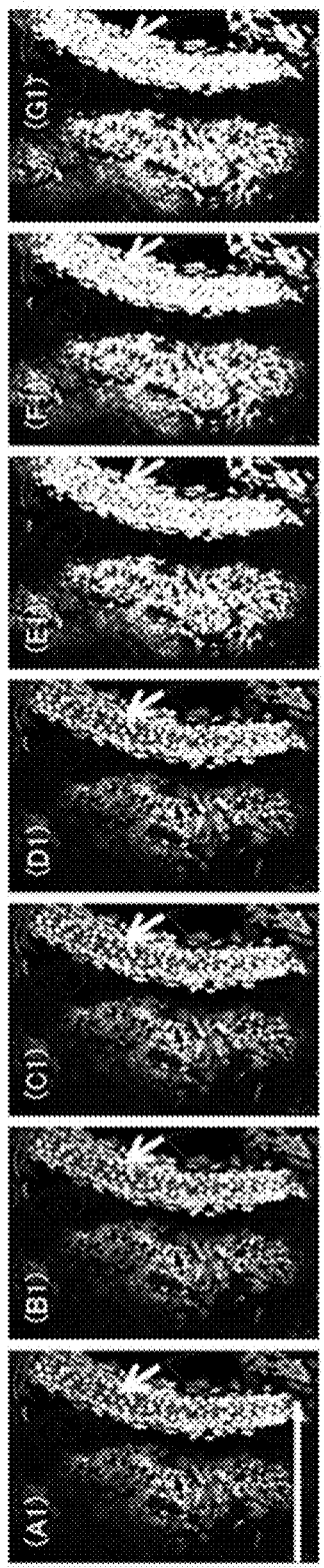

[Fig. 10]
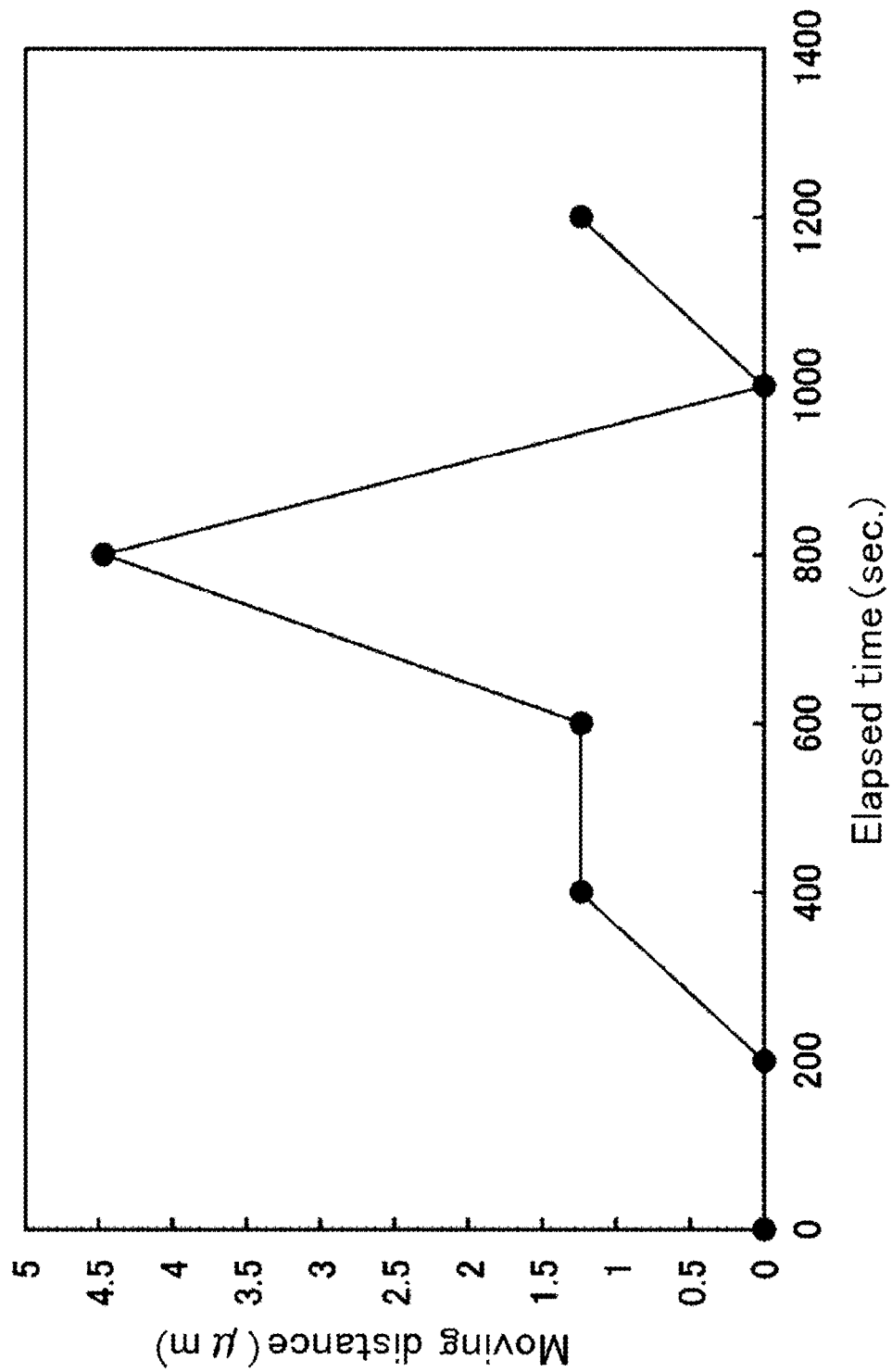

[Fig. 11]
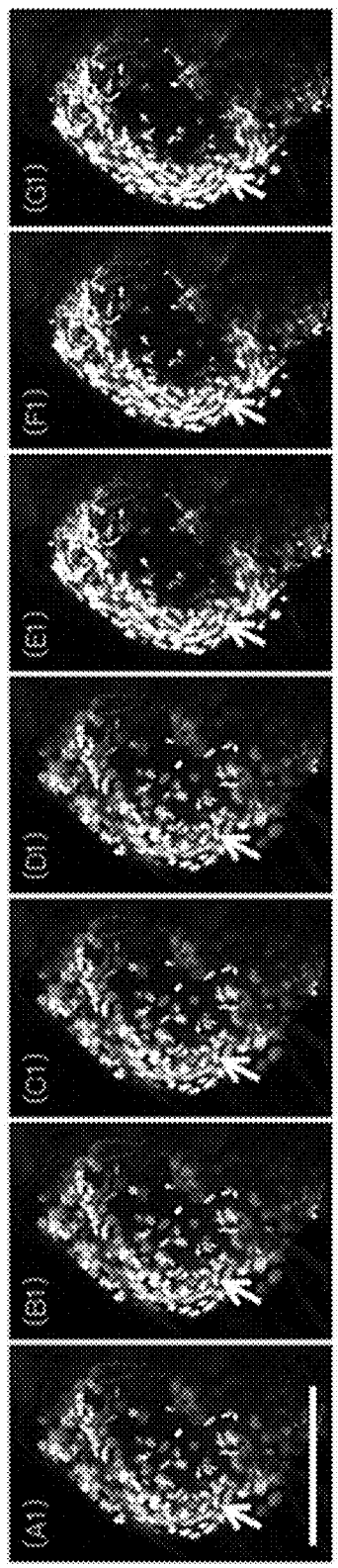

[Fig. 12]
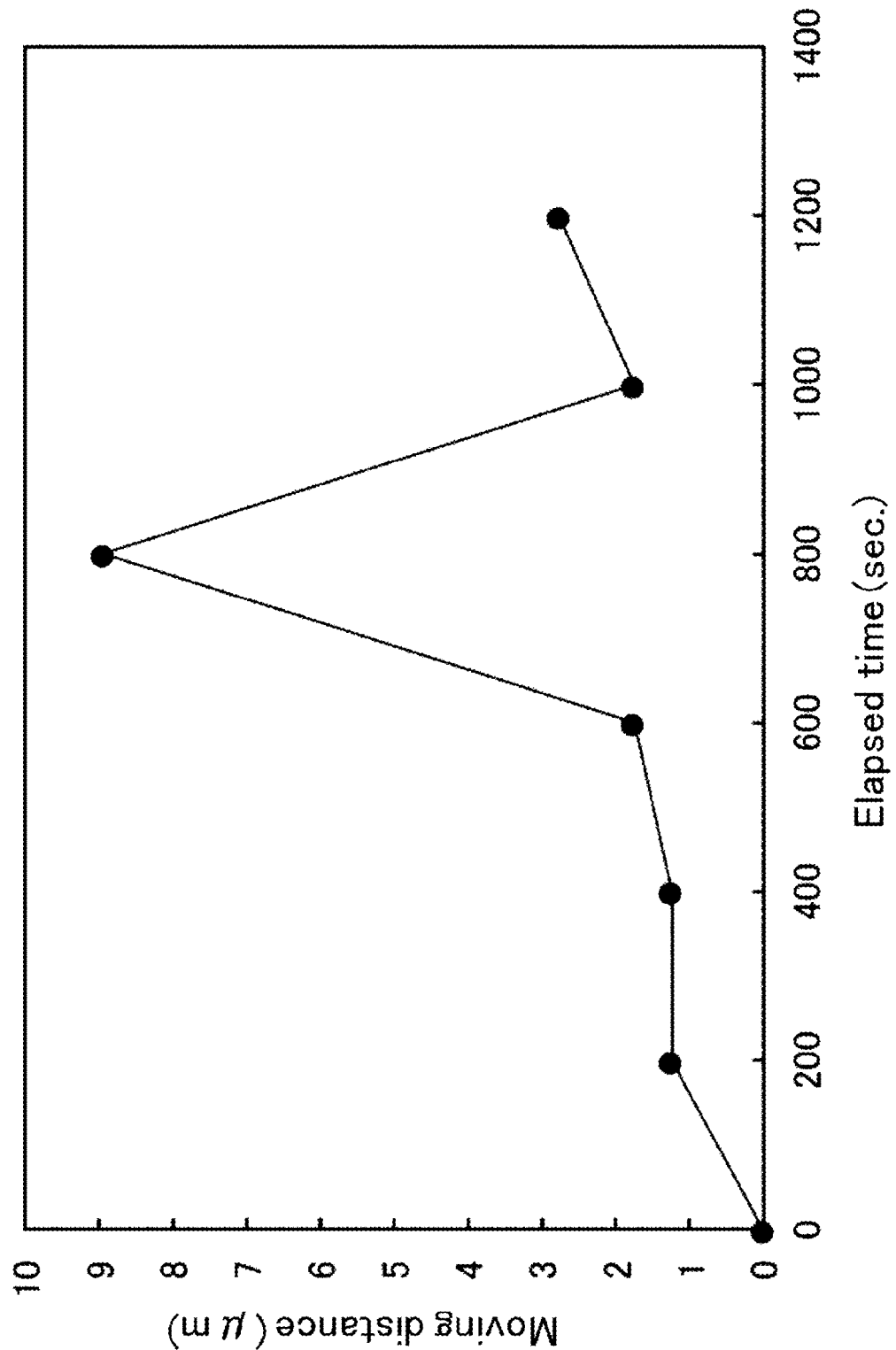

[Fig. 13]
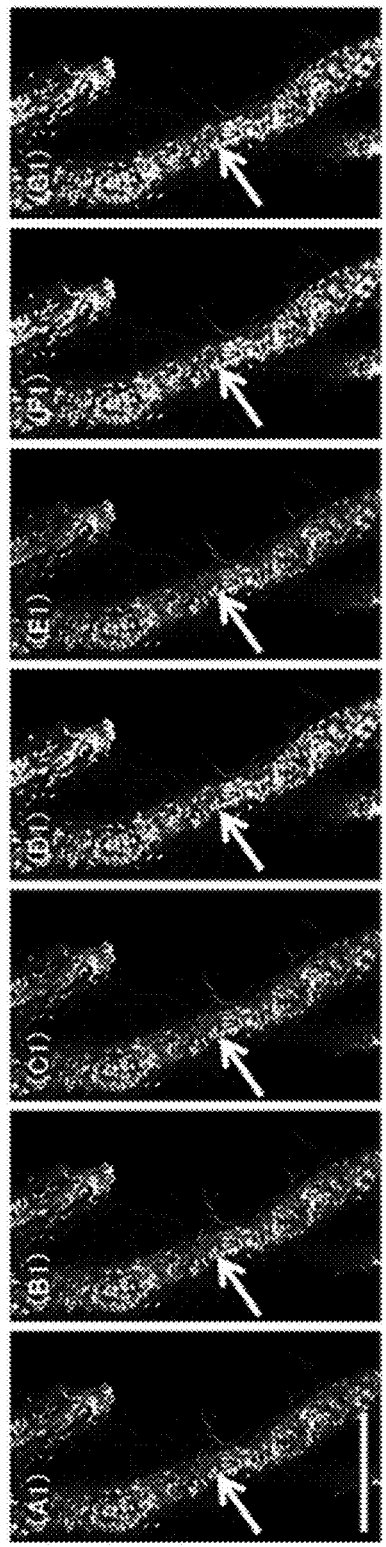

[Fig. 14]
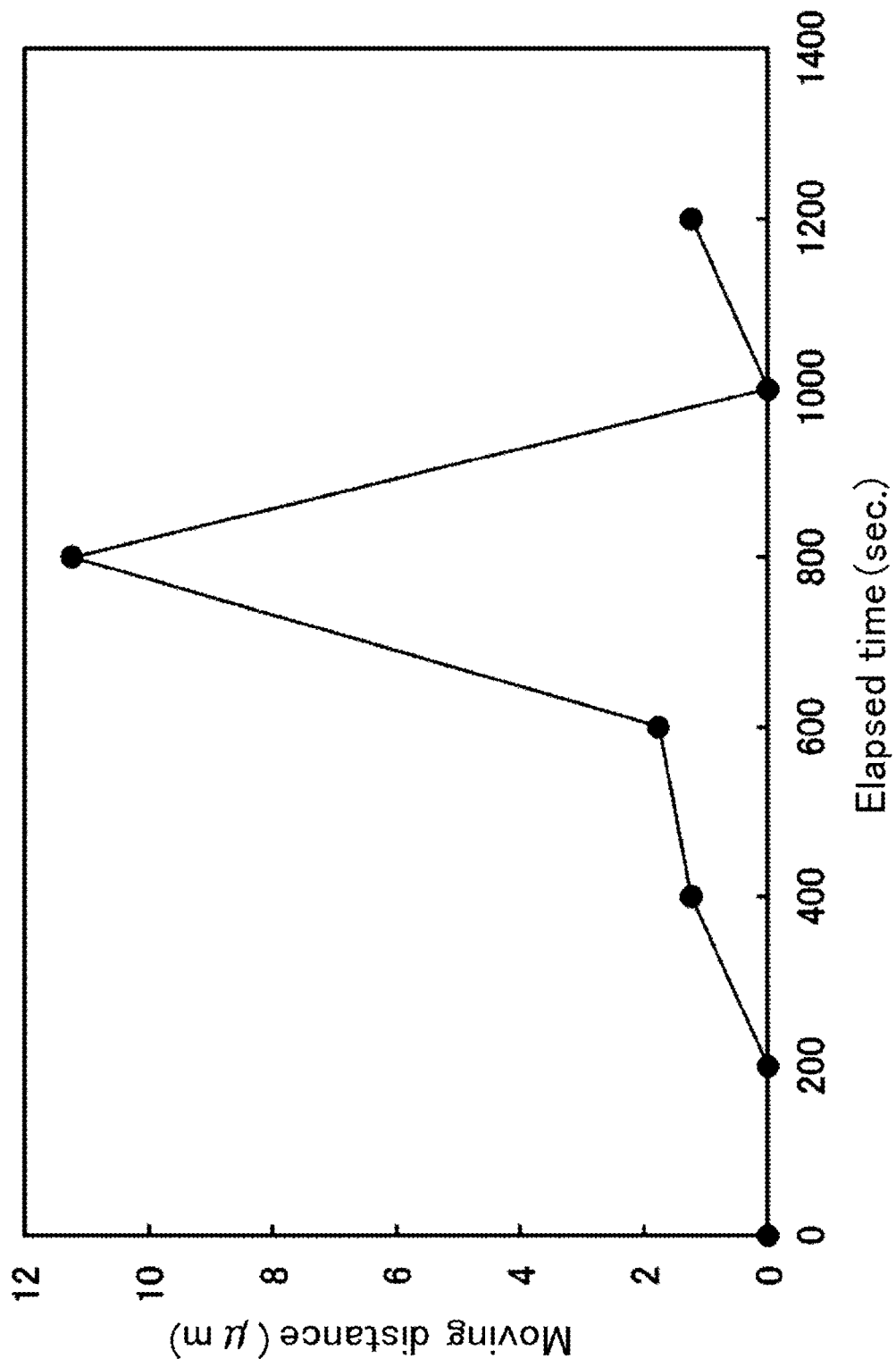

[Fig. 15]
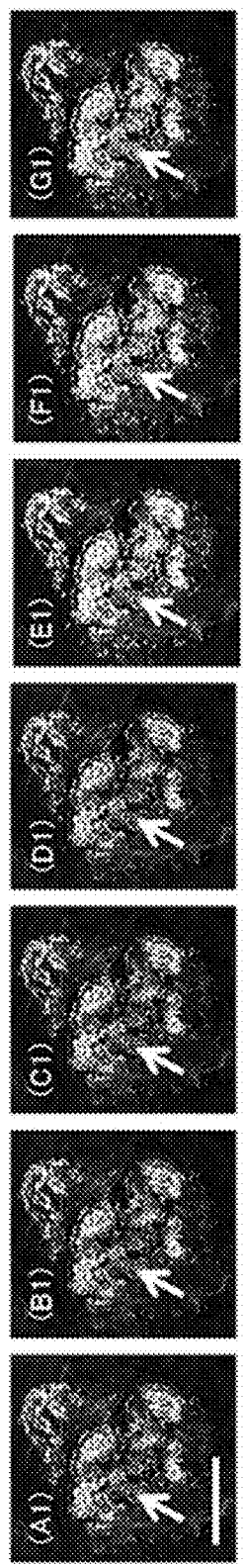

[Fig. 16]
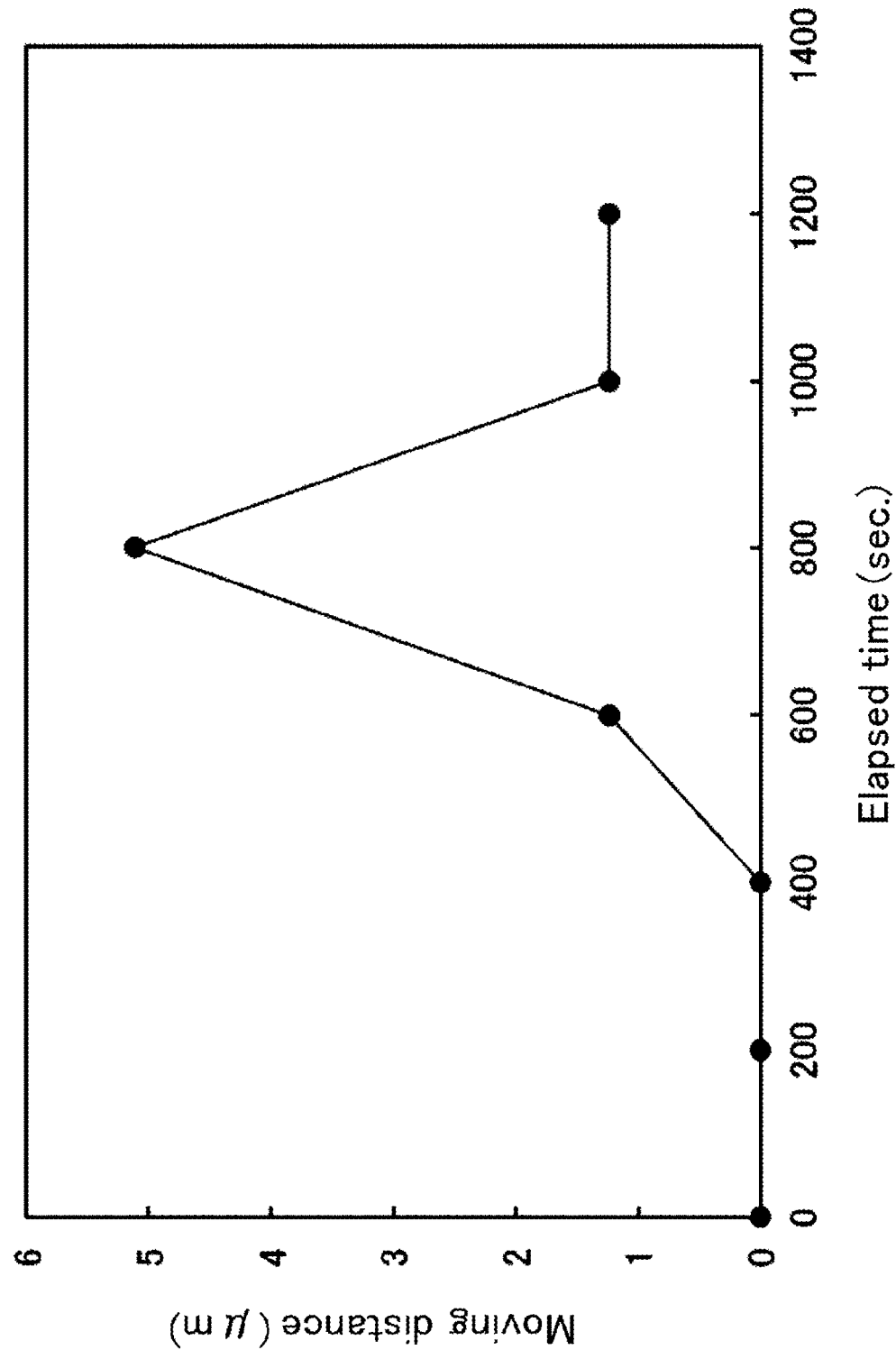

[Fig. 17]
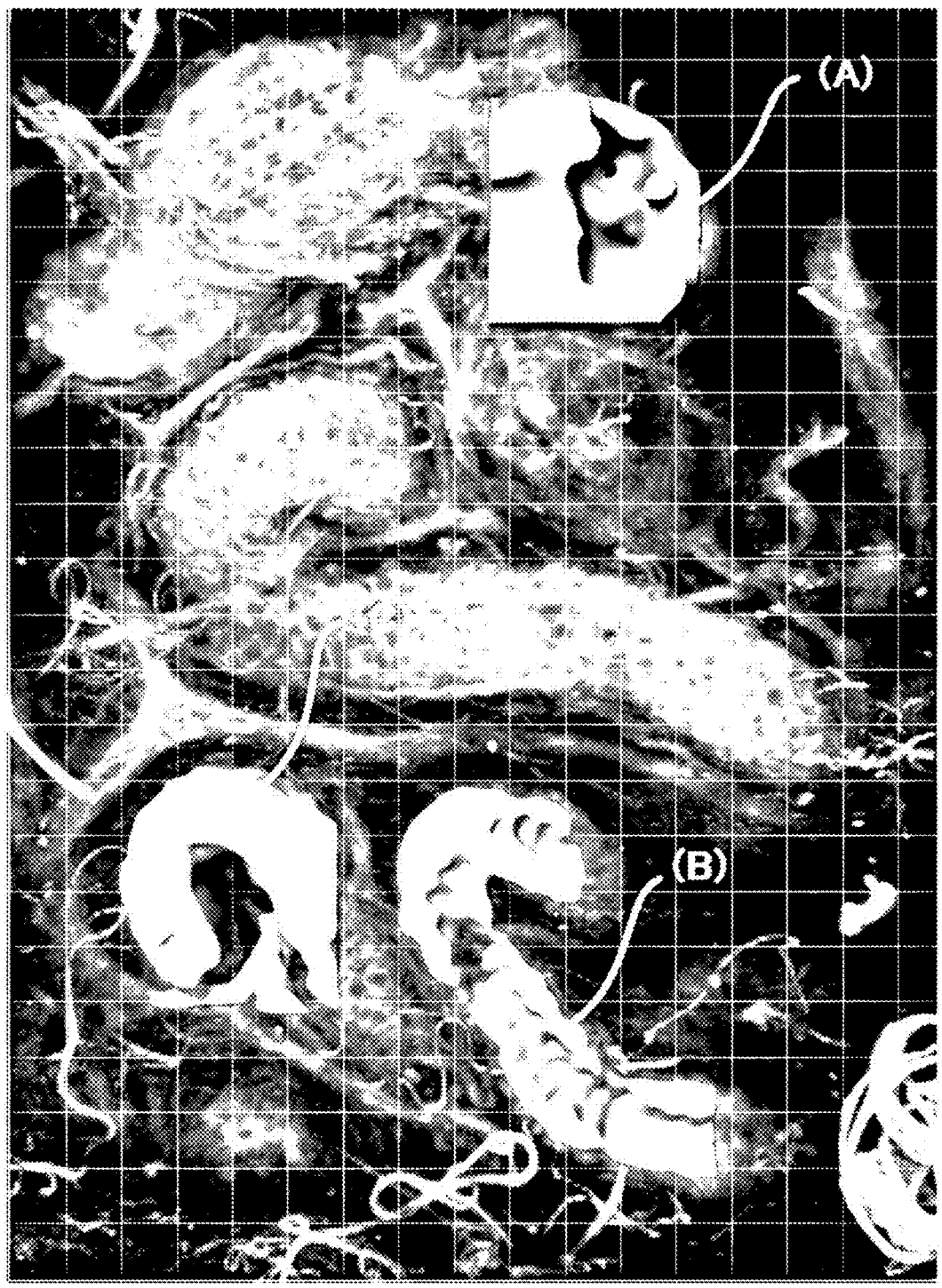

[Fig. 18]
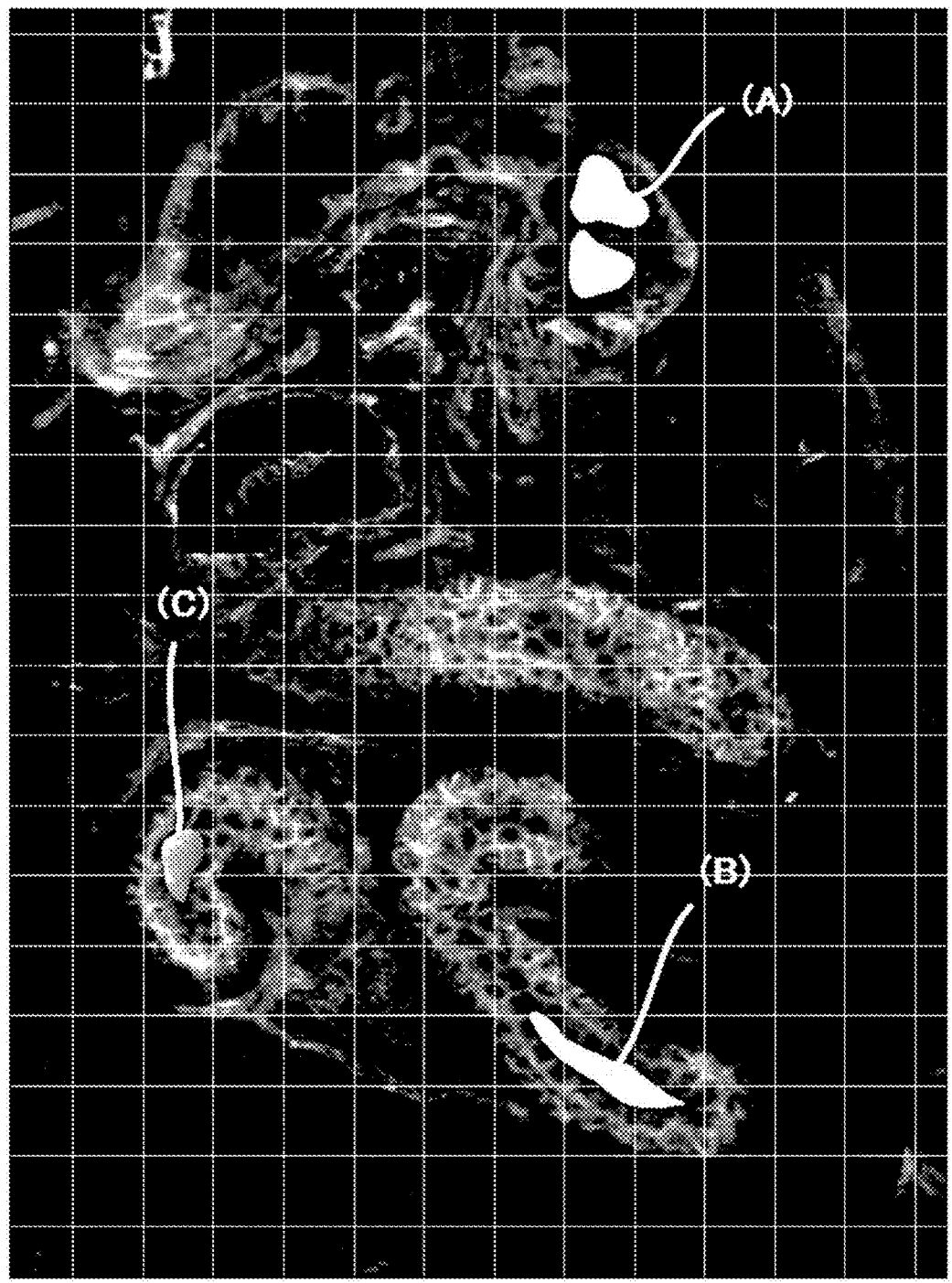

[Fig. 19]
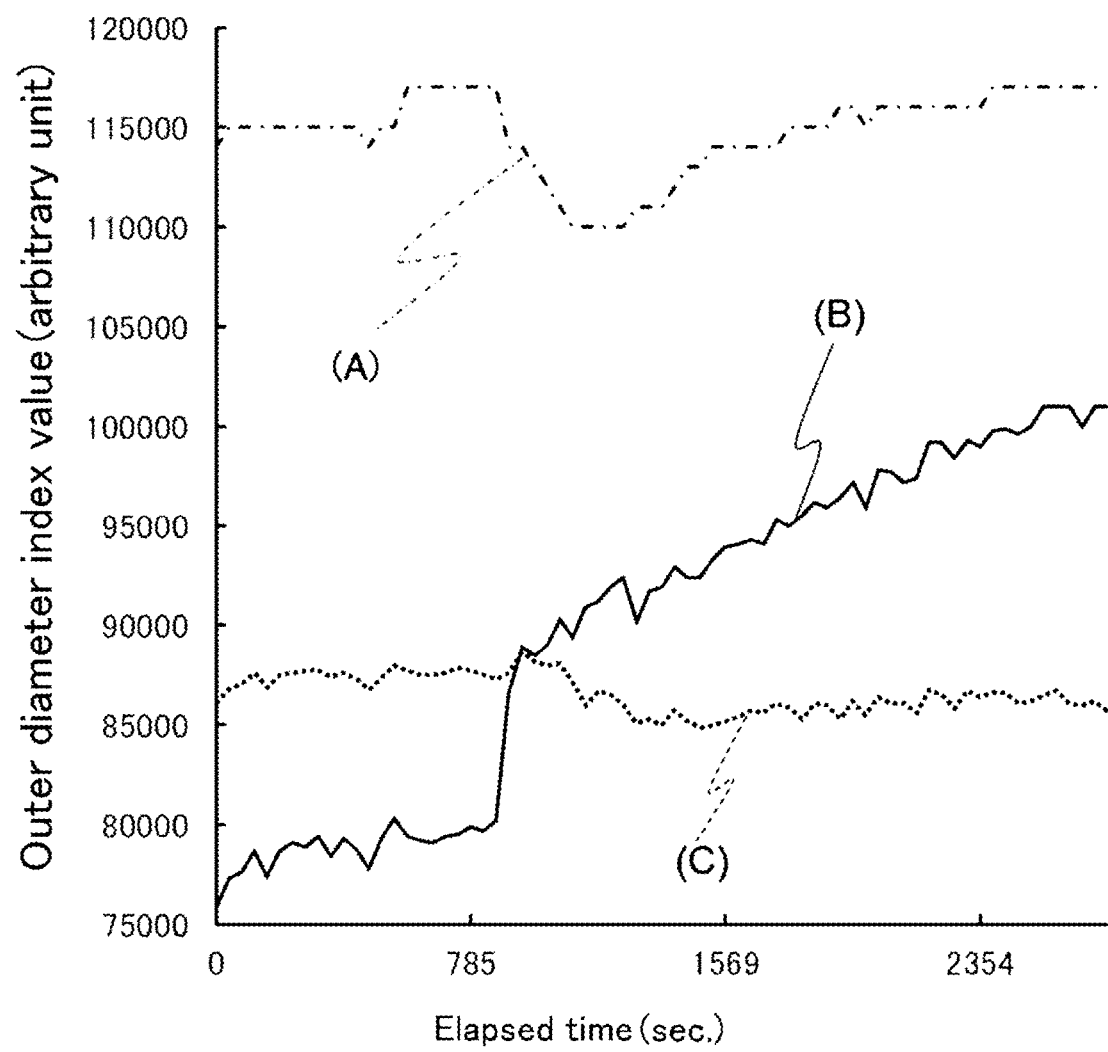

[Fig. 20]
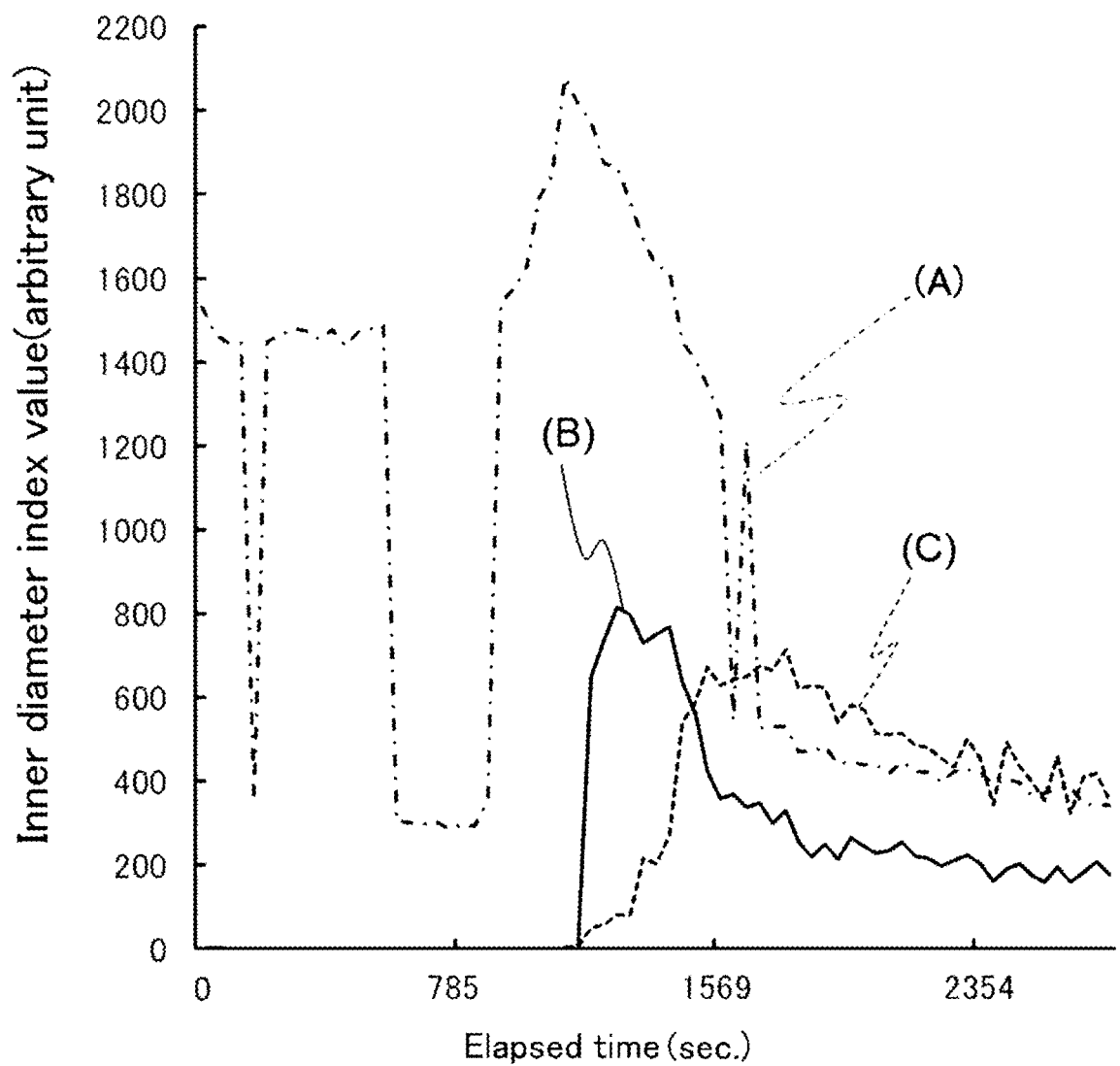

[Fig. 21]
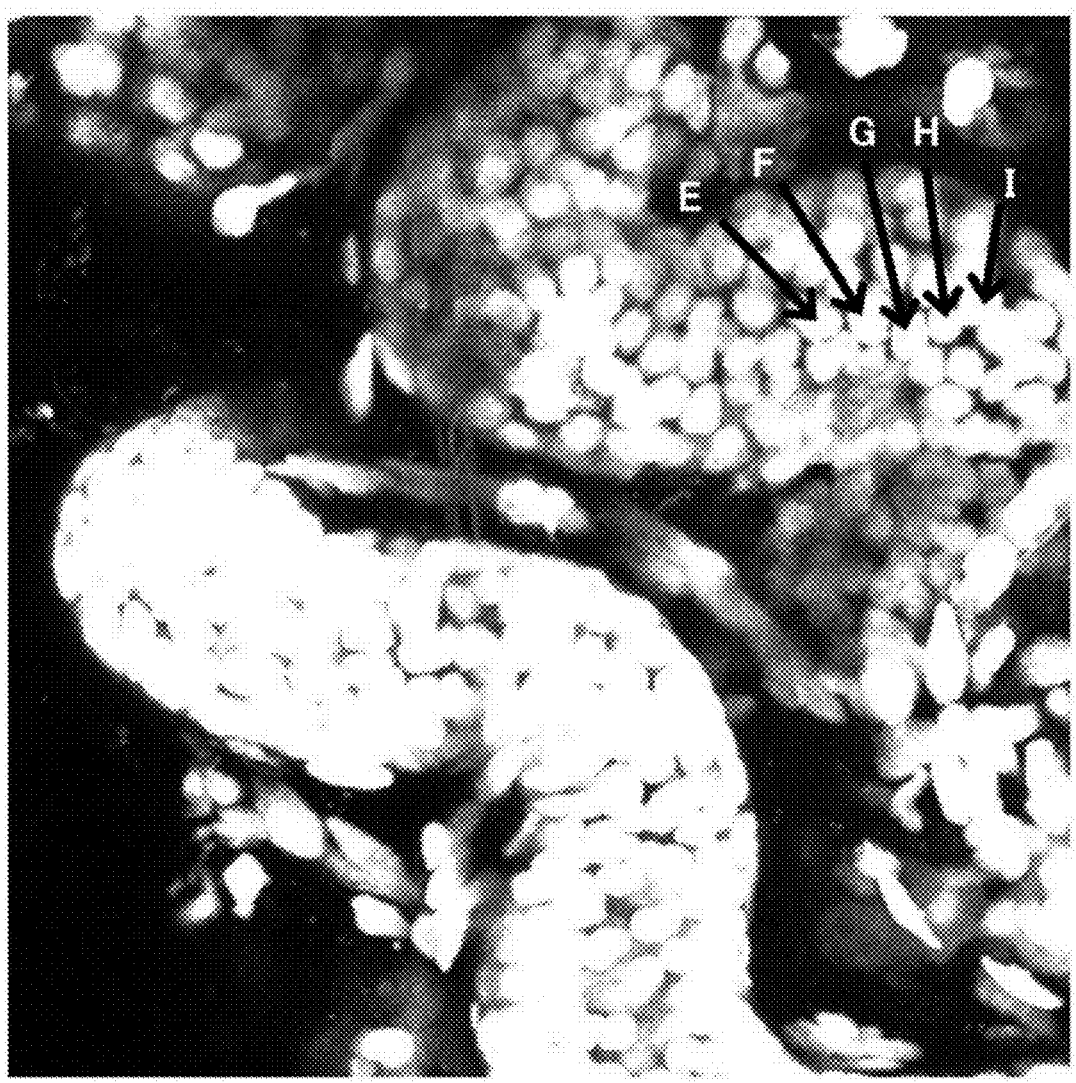

[Fig. 22]

[Fig. 23]
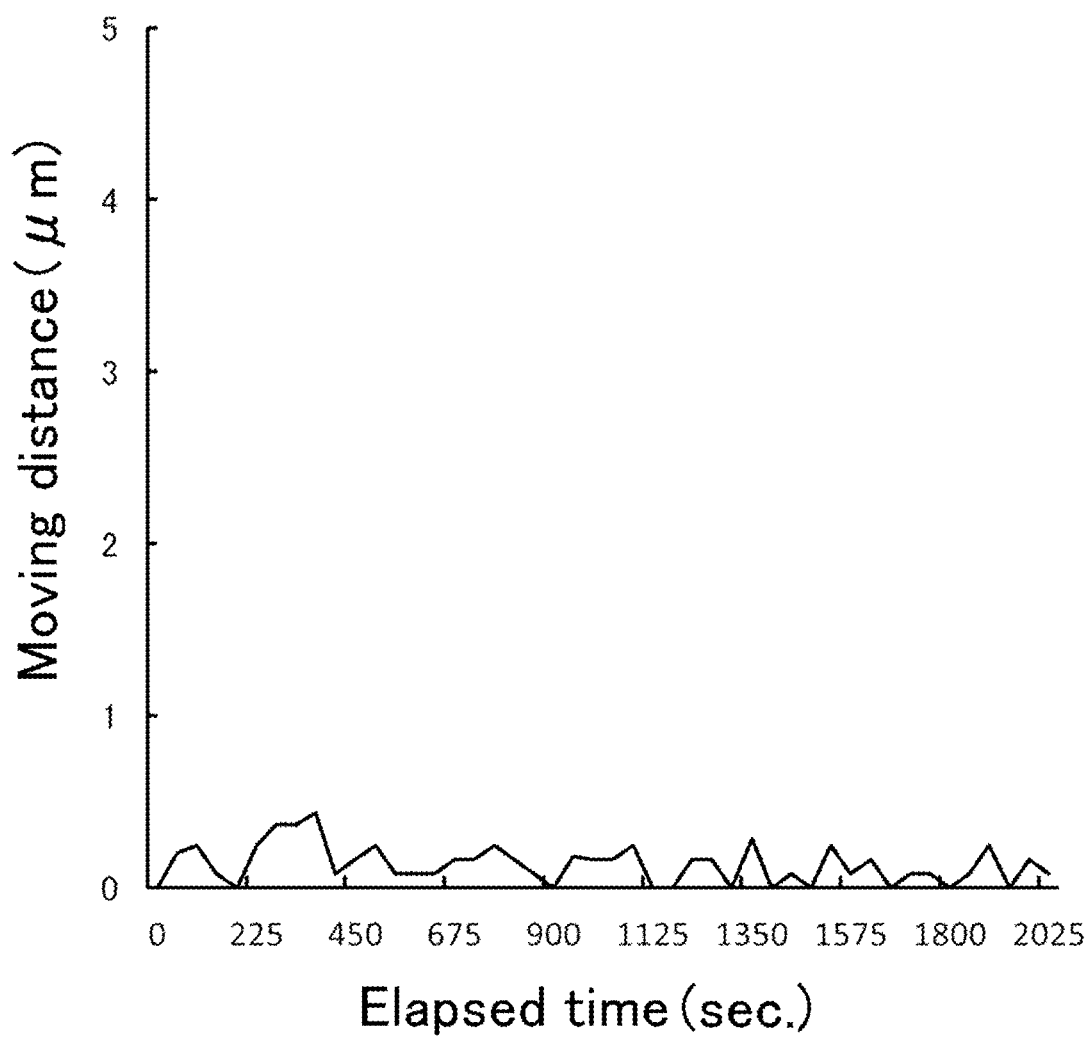

[Fig. 24]
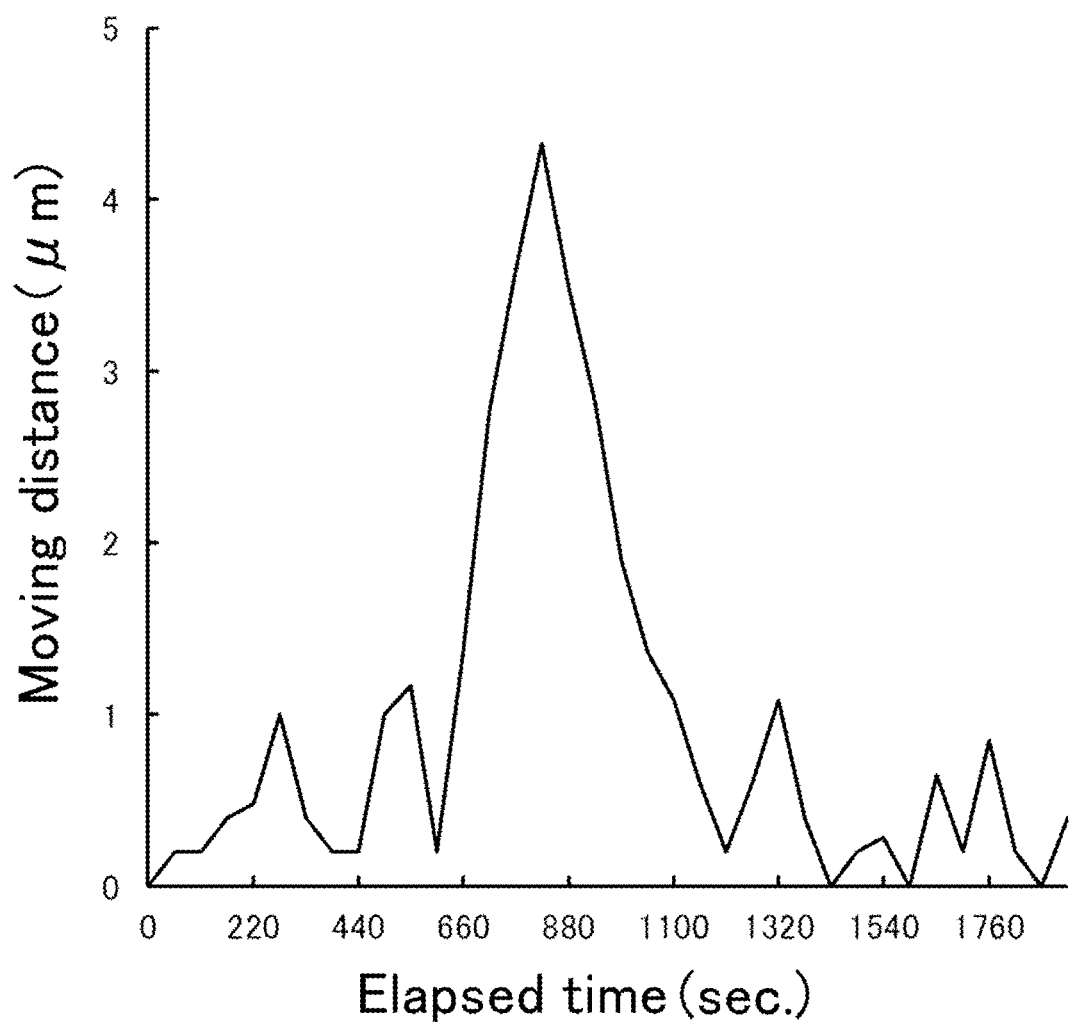

METHOD FOR OBSERVING DYNAMICS OF SWEAT GLANDS

TECHNICAL FIELD

The present invention relates to a method for observing dynamics of a sweat gland. More specifically, the present invention relates to a method for observing dynamics of a sweat gland and a method for evaluating a test substance, which are useful for development of an external preparation such as a cosmetic.

BACKGROUND ART

Excessive perspiration can cause skin stickiness and discomfort. An antiperspirant including a component which blocks a sweat gland to suppress perspiration, and the like have been developed. However, with rise in cleanliness in recent years, it has been demanded to more effectively suppress excessive perspiration and the like. In order to develop a component which suppresses excessive perspiration and the like more effectively, a technique for observing a condition of a sweat gland has been required.

On the other hand, it has been known that keratin 5 is expressed in a sweat gland cell contained in a sweat gland (see, for example, Non-Patent Literature 1). However, the present inventors have not found a literature specifically describing a method for observing dynamics of a sweat gland, at present.

PRIOR ART LITERATURES

Non-Patent Literatures

Non-Patent Literature 1: Roland Moll et al., "Expression of keratin 5 as a distinctive feature of epithelial and biphasic mesotheliomas; An immunohistochemical study using monoclonal antibody AE14", Virchows Archiv B cell Pathology Including Molecular Pathology, published in 1989, Vol. 58, pp. 129-145

SUMMARY OF THE INVENTION

Problems to be Solved by the Invention

The present invention has been accomplished in view of the above-mentioned prior arts. An object of the present invention is to provide a method for observing dynamics of a sweat gland, which can accurately observe dynamics of a sweat gland in a living state, and a method for evaluating a test substance, which can easily evaluate a perspiration-controlling action possessed by the test substance.

Means for Solving the Problems

The gist of the present invention relates to:
(1) a method for observing dynamics of a sweat gland, including the steps of:
(A) staining an isolated whole sweat gland with at least one staining reagent selected from the group consisting of a staining reagent for a cell membrane, a staining reagent for a nucleus and a staining reagent for a cytoskeletal component,
(B) holding the whole sweat gland stained in the step (A) on a support with at least one material selected from the group consisting of collagen, agarose, basement membrane matrix, poly-D-lysine and a membrane so that the position of the whole sweat gland stained in the step (A) is retained, to obtain an observation sample, and
(C) observing dynamics of the whole sweat gland contained in the observation sample obtained in the step (B);
(2) the method for observing dynamics of a sweat gland according to the item (1), wherein a buffer is added onto the whole sweat gland held on the support in the step (B);
(3) the method for observing dynamics of a sweat gland according to the item (2), wherein the buffer is a buffer containing 100 to 150 mM sodium chloride, 3 to 7 mM potassium chloride, 0.5 to 2 mM calcium chloride, 0.5 to 2 mM magnesium chloride, 20 to 30 mM sodium bicarbonate, 0.5 to 2 mM sodium dihydrogen phosphate, 2 to 8 mM glucose and 5 to 15 mg/100 mL of a fatty acid-free bovine serum albumin, and having a pH of 7.1 to 7.6;
(4) the method for observing dynamics of a sweat gland according to any one of the items (1) to (3), wherein in the step (C), the whole sweat gland contained in the observation sample is contacted with a stimulant, and dynamics of the whole sweat gland caused by the stimulant is observed;
(5) a method for evaluating a test substance, wherein whether or not the test substance has a perspiration-controlling action is evaluated, the method including the steps of:
(a) staining an isolated whole sweat gland with at least one staining reagent selected from the group consisting of a staining reagent for a cell membrane, a staining reagent for a nucleus and a staining reagent for a cytoskeletal component,
(b) holding the whole sweat gland stained in the step (a) on a support with at least one material selected from the group consisting of collagen, agarose, basement membrane matrix, poly-D-lysine and a membrane so that the position of the whole sweat gland stained in the step (A) is retained, to obtain an observation sample,
(c) contacting the whole sweat gland contained in the observation sample with the test substance to observe dynamics of the whole sweat gland, and
(d) evaluating whether or not the test substance has a perspiration-controlling action, based on dynamics of the whole sweat gland observed in the step (c);
(6) the method for evaluating a test substance according to the item (5), wherein in the step (b), a buffer is added onto the whole sweat gland held on the support;
(7) the method for evaluating a test substance according to the item (6), wherein the buffer is a buffer containing 100 to 150 mM sodium chloride, 3 to 7 mM potassium chloride, 0.5 to 2 mM calcium chloride, 0.5 to 2 mM magnesium chloride, 20 to 30 mM sodium bicarbonate, 0.5 to 2 mM sodium dihydrogen phosphate, 2 to 8 mM glucose and 5 to 15 mg/100 mL of fatty acid-free bovine serum albumin, and having a pH of 7.1 to 7.6; and
(8) the method for evaluating a test substance according to any one of the items (5) to (7), wherein in the step (c), the whole sweat gland contained in the observation sample is contacted with the test substance and a stimulant, and the dynamics of the whole sweat gland is observed.

Effects of the Invention

According to the method for observing dynamics of a sweat gland of the present invention, there are exhibited excellent effects such that dynamics of a sweat gland in a living state can be accurately observed. In addition, according to the method for evaluating a test substance of the present invention, there are exhibited excellent effects such that a perspiration-controlling action possessed by the test substance can be easily evaluated.

BRIEF DESCRIPTION OF THE DRAWINGS

FIG. 1 is a schematic explanation view showing a structure of a human sweat gland.

FIG. 2 is a photograph substituted for a drawing, showing results of dynamics of the sweat gland observed by time-lapse imaging based on fluorescence derived from a nuclear staining reagent and fluorescence derived from a cytoskeleton-staining reagent in Example 1.

FIG. 3 is a photograph substituted for a drawing, in which the panel (A1) shown in the photograph substituted for a drawing of FIG. 2 in Example 1 is enlarged.

FIG. 4 is a graph showing changes of a distance between two cells included in the sweat gland shown in the drawing-substituted photograph of FIG. 2 with the passage of time in Example 1.

FIG. 5 is a graph showing changes of a moving distance of each cell included in the sweat gland shown in the drawing-substituted photograph of FIG. 2 with the passage of time in Example 1.

FIG. 6 is a photograph substituted for a drawing, showing results of dynamics of the sweat gland observed by time-lapse imaging based on fluorescence derived from a nuclear staining reagent and fluorescence derived from a cell membrane-staining reagent in Example 2.

FIG. 7 is a photograph substituted for a drawing, showing results of dynamics of the sweat gland observed by time-lapse imaging based on fluorescence derived from a nuclear staining reagent in Example 3.

FIG. 8 is a graph showing changes of a moving distance of each cell included in the sweat gland shown in the drawing-substituted photograph of FIG. 7 with the passage of time in Example 3.

FIG. 9 is a photograph substituted for a drawing, showing results of dynamics of the sweat gland obtained in Example 4 observed by time-lapse imaging based on fluorescence derived from a nuclear staining reagent.

FIG. 10 is a graph showing changes of a moving distance of each cell included in the sweat gland shown in the drawing-substituted photograph of FIG. 9 with the passage of time in Example 4.

FIG. 11 is a photograph substituted for a drawing, showing results of dynamics of the sweat gland observed by time-lapse imaging based on fluorescence derived from a nuclear staining reagent in Example 5.

FIG. 12 is a graph showing changes of a moving distance of each cell included in the sweat gland shown in the drawing-substituted photograph of FIG. 11 with the passage of time in Example 5.

FIG. 13 is a photograph substituted for a drawing, showing results of dynamics of the sweat gland observed by time-lapse imaging based on fluorescence derived from a nuclear staining reagent in Example 6.

FIG. 14 is a graph showing changes of a moving distance of each cell included in the sweat gland shown in the drawing-substituted photograph of FIG. 13 with the passage of time in Example 6.

FIG. 15 is a photograph substituted for a drawing, showing results of dynamics of the sweat gland observed by time-lapse imaging based on fluorescence derived from a nuclear staining reagent in Example 7.

FIG. 16 is a graph showing changes of a moving distance of each cell included in the sweat gland shown in the drawing-substituted photograph of FIG. 15 with the passage of time in Example 7.

FIG. 17 is a photograph substituted for a drawing, showing sites where changes of outer diameter index values of tubules of sweat gland are determined with the passage of time in Example 8.

FIG. 18 is a photograph substituted for a drawing, showing sites where changes of inner diameter index values of tubules of sweat gland are determined with the passage of time in Example 8.

FIG. 19 is a graph showing changes of the outer diameter index values with the passage of time at the determined sites shown in the drawing-substituted photograph of FIG. 17 in Example 8.

FIG. 20 is a graph showing changes of inner diameter index values with the passage of time at the determined sites shown in the drawing-substituted photograph of FIG. 18 in Example 8.

FIG. 21 is a photograph substituted for a drawing, showing results of dynamics of the sweat gland of Experiment number 1 observed in Example 9.

FIG. 22 is a photograph substituted for a drawing, showing results of dynamics of the sweat gland of Experiment number 2 observed in Example 9.

FIG. 23 is a graph showing changes of a moving distance of each cell included in the sweat gland of Experiment number 1 with the passage of time in Example 9.

FIG. 24 is a graph showing changes of a moving distance of each cell included in the sweat gland of Experiment number 2 with the passage of time in Example 9.

MODE FOR CARRYING OUT THE INVENTION

The method for observing dynamics of a sweat gland according to the present invention includes the steps of:
(A) staining an isolated whole sweat gland with at least one staining reagent selected from the group consisting of a staining reagent for a cell membrane, a staining reagent for a nucleus and a staining reagent for a cytoskeletal component,
(B) holding the whole sweat gland stained in the step (A) on a support with at least one material selected from the group consisting of collagen, agarose, basement membrane matrix, poly-D-lysine and a membrane so that the position of the whole sweat gland stained in the step (A) is retained, to obtain an observation sample, and
(C) observing dynamics of the whole sweat gland contained in the observation sample obtained in the step (B).

A sweat gland 1 is composed of a secretory portion 2 and an excretory portion 3 connected to the secretory portion 2 as shown in the schematic explanation view showing a structure of a human sweat gland of FIG. 1. The secretory portion 2 is present in dermis 5 of skin 4. The secretory portion 2 is an entangled single tubular gland having a coil structure 6 which is twisted in a coil shape. A myoepithelial cell (not shown in the figure) is present on the surface of the secretory portion.

The provenance of the whole sweat gland is not particularly limited thereto. Among the sweat glands, a human sweat gland is preferred when the method for observing dynamics of a sweat gland according to the present invention is used for observing dynamics of a sweat gland during sweat secretion in human.

Incidentally, in the present description, the term "whole sweat gland" means a whole extent of a sweat gland. In addition, in the present description, the term "isolated whole sweat gland" means a whole sweat gland in a living state obtained from a skin tissue. The whole sweat gland can be partially lost.

The whole sweat gland is usually isolated from a skin tissue obtained within preferably 70 hours after being removed from the donor, and more preferably within 15 hours after being removed from the donor, from the viewpoint of accurate observation of dynamics of a sweat gland in a living state. In addition, it is preferred that the whole sweat gland is a sweat gland obtained within 10 hours after the isolation from the skin tissue.

In the present description, the term "living state" refers to a state showing biological activity and movement similar to the biological activity and movement in a living donor.

Examples of dynamics of a sweat gland include movement in contraction of a sweat gland and the like, and the present invention is not limited only to those exemplified ones.

In a conventional microscopic observation of a tissue obtained from a living organism, tissue fixation, optically transparent treatment of the tissue and the like are carried out before the tissue is stained. The tissue fixation is carried out in order to inhibit progress of a biochemical reaction in the tissue, so that change of morphology of cells included in the tissue is suppressed. However, when the tissue fixation and the optically transparent treatment are carried out, the obtained tissue is in a state of loss of biological activity, so that it is impossible to observe the dynamics of the tissue. In contrast, in the method for observing dynamics of a sweat gland according to the present invention, the isolated whole sweat gland is stained in a living state in the step (A). Furthermore, in the method for observing dynamics of a sweat gland according to the present invention, an observation sample is obtained in the step (B) by holding the stained whole sweat gland in a living state on a support with at least one material selected from the group consisting of collagen, agarose, basement membrane matrix, poly-D-lysine and a membrane so that the position of the stained whole sweat gland is retained. As described above, the method for observing dynamics of a sweat gland according to the present invention enables to accurately observe dynamics of a sweat gland, since both the step (A) and the step (B) are employed.

In the step (A), the isolated whole sweat gland is stained with the staining reagent. The isolated whole sweat gland can be stained by contacting the isolated whole sweat gland with the staining reagent. Thus, at least one material of a cell membrane, a nucleus and a cytoskeleton component included in the whole sweat gland allows to bind with the corresponding staining reagent, to obtain a whole sweat gland stained with the staining reagent.

The staining reagent for a cell membrane (hereinafter also referred to as "cell membrane-staining reagent") includes a substance which specifically binds to a cell membrane marker (hereinafter also referred to as "cell membrane-binding substance") and a detectable substance. The cell membrane-staining reagent can contain a substance which serves as a cell membrane-binding substance and as a detectable substance.

Examples of the cell membrane marker include a cell membrane kinase and the like, and the present invention is not particularly limited thereto. The cell membrane-binding substance can be any substance that binds to a cell membrane in a living state.

Examples of the cell membrane-binding substance include an anti-cell membrane marker antibody such as an anti-cell membrane kinase antibody or an antibody fragment thereof; a compound specifically binding to a cell membrane marker, such as a lectin binding to a carbohydrate chain of the cell membrane, and the like, and the present invention is not limited only to those exemplified ones.

Examples of the detectable substance contained in the cell membrane-staining reagent include a fluorescent dye molecule such as Alexa fluor series including a fluorescent dye molecule manufactured by Molecular Probes Inc. under the trade name of Alexa fluor 488; a fluorescent substance such as Cy5, and the like, and the present invention is not limited only to those exemplified ones.

In the present invention, the antibody can be a monoclonal antibody or a polyclonal antibody.

The staining reagent for a nucleus (hereinafter also referred to as "nuclear staining reagent") contains a substance specifically binding to a nucleus component (hereinafter also referred to as "nucleus-binding substance"), and a detectable substance. The nuclear staining reagent can contain a detectable nucleus-binding substance.

Examples of the nucleus component include a nucleic acid such as DNA, and the like, and the present invention is not limited only to those exemplified ones. The nucleus-binding substance can be a cell membrane-permeating substance. Examples of the nucleus-binding substance include Hoechst 33342 and the like, and the present invention is not limited only to those exemplified ones.

Examples of the detectable substance contained in the nuclear staining reagent include a fluorescent substance such as 4',6-diamidino-2-phenylindole; a fluorescent dye such as Hoechst series including Hoechst 33342, and the like, and the present invention is not limited only to those exemplified ones. The nucleus-binding substance Hoechst 33342 can be used as a fluorescent substance.

A staining reagent for a cytoskeletal component (hereinafter also referred to as "cytoskeleton-staining reagent") contains a substance specifically binding to the cytoskeletal component (hereinafter also referred to as "cytoskeleton-binding substance"), and a detectable substance. The cytoskeleton-staining reagent can contain a substance which serves as a cytoskeleton-binding substance and as a detectable substance.

Examples of the cytoskeletal component include a contractile protein such as actin or myosin; an intermediate filament such as keratin; a microtubule-constituting protein such as tubulin, and the like, and the present invention is limited only to those exemplified ones.

The cytoskeleton-binding substance can be any substance which binds to a cell membrane in a living state. Examples of the cytoskeleton-binding substance include an anti-cytoskeletal component antibody such as an anti-actin antibody, an anti-myosin antibody, an anti-keratin antibody, an anti-tubulin antibody or an antibody fragment of each of these antibodies; a compound specifically binding to a cytoskeletal component including phalloidin, and the like, and the present invention is not particularly limited only to the exemplified ones.

Examples of the detectable substance contained in the cytoskeleton-staining reagent include a fluorescent substance such as a fluorescent dye such as Alexa fluor series including fluorescent dye molecules manufactured by Molecular Probes Inc. under the trade names of Alexa fluor 488 and Alexa fluor 555, and the like, and the present invention is not limited only to those exemplified ones.

When the nucleus, the cell membrane and the cytoskeleton are simultaneously visualized in distinction from each other, it is preferred that the detectable substance contained in the nuclear staining reagent, the detectable substance contained the cell membrane-staining reagent and the detectable substance contained the cytoskeleton-staining reagent are substances which generate signals having a wavelength different from each other.

Examples of the cell membrane-staining reagent include a reagent manufactured by Thermo Fisher Scientific Co., Ltd. under the trade name of CellMask, and the like, and the present invention is not limited only to those exemplified ones. Examples of the cytoskeleton-staining reagent include Hoechst 33342 and the like, and the present invention is not limited only to those exemplified ones. Examples of the cytoskeleton-staining reagent include reagents manufactured by Cytoskelton under the trade names of Acti-stain 488 and Acti-stain 555, and the like, and the present invention is limited only to those exemplified ones.

When the isolated whole sweat gland is contacted with the staining reagent, the mixing ratio and the contact duration between the isolated whole sweat gland and the staining reagent cannot be absolutely determined because the mixing ratio and the contact duration vary depending on the kind of the staining reagent and the like. It is therefore preferred to appropriately adjust the mixing ratio and the contact duration in accordance with the kind of the staining reagent and the like.

From the viewpoint of more accurate observation of dynamics of a sweat gland, after contacting the isolated whole sweat gland with the staining reagent, it is preferred that the stained whole sweat gland is washed with an appropriate washing solution. Examples of the washing solution include a phosphate-buffered physiological saline, a phosphate buffer and the like, and the present invention is not limited only to those exemplified ones.

It is preferred that the stained whole sweat gland is subjected to a blocking treatment using a blocking agent from the viewpoint of more accurate observation of dynamics of a sweat gland when the staining reagent contains an antibody or an antibody fragment thereof. Examples of the blocking agent include a phosphate-buffered physiological saline containing albumin and the like, and the present invention is not limited only to those exemplified ones.

Next, in the step (B), the whole sweat gland stained in the step (A) is held on a support with at least one material selected from the group consisting of collagen, agarose, basement membrane matrix, poly-D-lysine and a membrane so that the position of the whole sweat gland stained in the step (A) is retained. In the step (B), it is preferable to add a buffer onto the sweat gland held on the support from the viewpoint of suppression of drying of the sweat gland held on the support. Thus, an observation sample including a sweat gland is obtained in a living state.

The observation sample allows to perform accurate observation of movement of a sweat gland including contraction of a sweat gland while movement not related to dynamics of a sweat gland itself is suppressed during observation of dynamics of a sweat gland, since the observation sample has a sweat gland in a living state held on the support so that the position of the sweat gland is retained. Accordingly, the observation sample is suitable for observing dynamics of a sweat gland with an optical microscope such as a fluorescence microscope or a confocal laser microscope.

Examples of the collagen include type I collagen such as collagen type I-A or collagen type I-B; type III collagen; type IV collagen, and the like, and the present invention is limited only to those exemplified ones. When the collagen is used in the step (B), the stained whole sweat gland can be held on the support, for example, by dropping a collagen-containing liquid cooled on ice to the stained whole sweat gland placed on the support, and then incubating the whole sweat gland placed on the support at 22 to 38° C. to gelate the collagen, or the like.

The agarose can be agarose having a melting point at which a sweat gland-constituting cell is survived. When the agarose is used in the step (B), the stained whole sweat gland can be held on the support, for example, by dropping an agarose having a molten state onto the stained whole sweat gland on the support, and then incubating the whole sweat gland at a temperature equal to or lower than the melting point of the agarose to gelate the agarose, or the like.

The basement membrane matrix can contain laminin, collagen type IV, nidogen and heparan sulfate proteoglycan as an essential component. Examples of the basement membrane matrix include a product manufactured by Corning under the trade name of Matrigel® Growth Factor Reduced (GFR) Basement Membrane Matrix, and the like, and the present invention is not limited only to those exemplified ones. When the basement membrane matrix is used in the step (B), the stained whole sweat gland can be held on the support, for example, by dropping the basement membrane matrix onto the stained whole sweat gland placed on the support, and then incubating the stained whole sweat gland at 22 to 37° C. to gelate the basement membrane matrix, or the like.

The poly-D-lysine can have a molecular weight enough to adhere the sweat gland-constituting cell to the support. When the poly-D-lysine in the step (B), the stained whole sweat gland can be held on the support, for example, by coating the surface of the support with the poly-D-lysine, and then placing the whole sweat gland stained on the poly-D-lysine coated surface, or the like. A substance for enhancing the adhesiveness between the poly-D-lysine and the whole sweat gland, for example, laminin and the like can be further used from the viewpoint of enhancement of the adhesiveness between the poly-D-lysine and the whole sweat gland and suppression of the positional shift of the whole sweat gland.

The membrane can be a membrane having pores through which a buffer, a stimulant described below and a test substance described below can be passed, and the whole sweat gland cannot be passed. The pore diameter is preferably 40 μm or less, and more preferably 0.4 μm or less, from the viewpoint of suppression of passage of the whole sweat gland, and is preferably 0.1 μm or more from the viewpoint of allowing a stimulating agent described below or the like to pass through. When the membrane is used in the step (B), the stained whole sweat gland can be held on the support, for example, by placing the stained whole sweat gland on the support, and then placing the membrane on the stained whole sweat gland placed on the support.

Examples of the buffer include a buffer containing 120 to 160 mM sodium chloride, 3 to 7 mM potassium chloride, 1 to 3 mM calcium chloride, 1 to 3 mM magnesium chloride, 8 to 12 mM HEPES buffer and 8 to 12 mM glucose, and having a pH of 7.1 to 7.6 (hereinafter referred to as "buffer A"); a buffer containing 100 to 150 mM sodium chloride, 3 to 7 mM potassium chloride, 0.5 to 2 mM calcium chloride, 0.5 to 2 mM magnesium chloride, 20 to 30 mM sodium bicarbonate, 0.5 to 2 mM sodium dihydrogen phosphate, 2 to 8 mM glucose and 5 to 15 mg/100 mL of fatty acid-free bovine serum albumin, and having a pH of 7.1 to 7.6 (hereinafter referred to as "buffer B"); an isotonic solution such as a phosphate-buffered physiological saline, and the like, and the present invention is not limited only to those exemplified ones. Examples of the buffer A include an extracellular solution and the like, and the present invention is not particularly limited thereto. Examples of the buffer B include Krebs-Ringer's solution and the like, and the present invention is not limited only to those exemplified ones. Among these buffers, the buffer A, the buffer B and the phosphate-buffered physiological saline are preferable, the buffer B is more preferable, and the Krebs-Ringer's solution is furthermore preferable, since stimulation of the sweat gland with the stimulant can be favorably observed. The use of the buffer B, preferably the Krebs-Ringer's solution as the buffer enables to observe movement of the sweat gland in the absence of the stimulant.

Thereafter, in the step (C), dynamics of the whole sweat gland contained in the observation sample obtained in the step (B) is observed.

Dynamics of the whole sweat gland can be observed by using, for example, an optical microscope such as a fluorescence microscope or a confocal laser microscope, and the like. Concretely, the dynamics of the whole sweat gland can be observed, for example, by directly subjecting the stained whole sweat gland to live observation, by detecting and observing a signal derived from the staining reagent in the stained whole sweat gland, and the like. The dynamics of the whole sweat gland can be evaluated, for example, by using as an index, a change of a moving distance of a specific cell with the passage of time, a change of a distance between specific cells with the passage of time, a change of the volume of the tubule of the sweat gland with the passage of time, a change of an outer diameter of the tubule of included in the sweat gland with the passage of time, a change of an inner diameter of the tubule of included in the sweat gland with the passage of time, and the like.

The method for observing the dynamics of a sweat gland according to the present invention can further include a step of contacting the whole sweat gland with the stimulant, to observe dynamics of the whole sweat gland caused by the stimulant (hereinafter also referred to as "stimulant contacting step"). The stimulant contacting step can be carried out between the steps (B) and (C), or can be carried out during the step (C). It is preferred that the stimulant contacting step is carried out during the step (C) from the viewpoint of more accurate observation of dynamics of the sweat gland, particularly the contraction of the sweat gland.

Examples of the stimulant include a cholinergic agonist, an adrenergic agonist and the like, and the present invention is not limited only to those exemplified ones. Examples of the cholinergic agonist include acetylcholine, pilocarpine, bethanechol, carbachol and the like, and the present invention is not limited only to those exemplified ones. Examples of the adrenergic agonist include a catecholamine such as adrenaline, noradrenaline or dopamine, and the like, and the present invention is not limited only to those exemplified ones.

As explained above, the method for observing dynamics of a sweat gland according to the present invention include a procedure including the steps of staining an isolated whole sweat gland with at least one staining reagent selected from the group consisting of a cell membrane-staining reagent, a nuclear staining reagent and a cytoskeleton-staining reagent, and holding the stained whole sweat gland on a support with at least one material selected from the group consisting of collagen, agarose, basement membrane matrix, poly-D-lysine and a membrane so that the position of the sweat gland is retained, to obtain an observation sample. The method for observing dynamics of a sweat gland according to the present invention enables to observe movement during contraction of a sweat gland and the like, since the method does not need to perform tissue fixation, transparency treatment of the living tissue and the like, which inhibit progress of a biochemical reaction of a living tissue. In addition, the contraction of a sweat gland is also thought to be related to perspiration. Thus, it is expected that the method for observing dynamics of a sweat gland according to the present invention is used for screening or evaluation of a perspiration controlling component such as an antiperspirant component or a perspiration component, based on dynamics of a sweat gland. It is therefore expected that the method for observing dynamics of a sweat gland according to the present invention is used for development of an external preparation such as a cosmetic.

According to the method for observing dynamics of a sweat gland according to the present invention, there can be evaluated whether or not a test substance has a perspiration-controlling action. According to the method for observing dynamics of a sweat gland according to the present invention, for example, whether or not the test substance has a perspiration-controlling action can be evaluated by contacting a sweat gland with a test substance to observe dynamics of the sweat gland.

The method for evaluating a test substance according to the present invention is a method for evaluating a test substance, wherein whether or not the test substance has a perspiration-controlling action is evaluated. The method for evaluating a test substance according to the present invention includes the steps of:

(a) staining an isolated whole sweat gland with at least one staining reagent selected from the group consisting of a staining reagent for a cell membrane, a staining reagent for a nucleus and a staining reagent for a cytoskeletal component, (b) holding the whole sweat gland stained in the step (a) on a support with at least one material selected from the group consisting of collagen, agarose, basement membrane matrix, poly-D-lysine and a membrane so that the position of the whole sweat gland stained in the step (a) is retained, to obtain an observation sample, (c) contacting the whole sweat gland contained in the observation sample obtained in the step (b) with the test substance to observe dynamics of the whole sweat gland, and (d) evaluating whether or not the test substance has a perspiration-controlling action based on dynamics of the whole sweat gland observed in the step (c). In the present description, "perspiration-controlling action" includes "antiperspirant action" and "perspiration-inducing action". The "antiperspirant action" means an action of suppressing perspiration. The "perspiration-inducing action" means an action of perspiration or an action of promoting perspiration.

The step (a) and the step (b) can be carried out by methods similar to those carried out in the step (A) and the step (B) employed in the above-mentioned method for observing dynamics of a sweat gland.

In the step (c), the whole sweat gland contained in the observation sample obtained in the step (b) is contacted with the test substance to observe dynamics of the whole sweat gland.

Examples of the test substance include a substance which is expected to have a perspiration-controlling action, and the present invention is not limited only to those exemplified ones. Concrete examples of the test substance include an inorganic compound, an organic compound and the like, and the present invention is not limited only to those exemplified ones. The test substance can be used as it is or can be used by dissolving in a solvent as occasion demands. Examples of the solvent include a buffer which is used in the method for observing dynamics of a sweat gland according to the present invention, a physiological saline solution, water and the like, and the present invention is not limited only to those exemplified ones.

The whole sweat gland contained in the observation sample can be contacted with the test substance, for example, by adding a solution containing the test substance (hereinafter also referred to as "test solution") to the whole sweat gland placed on the observation sample and incubating the observation sample.

When the whole sweat gland contained in the observation sample is contacted with the test substance, the amount of the test substance to be contacted with the whole sweat gland, and the contact duration cannot be absolutely determined because the amount of the test substance to be contacted with the whole sweat gland and the contact duration vary depending on the kind of the test substance and the like. It is therefore preferred to appropriately adjust the amount of the test substance to be contacted with the whole sweat gland and the contact duration in accordance with the kind of the test substance and the like.

The content of the test substance in the test solution cannot be absolutely determined because the content of the test substance in the test solution varies depending on the kind of the test substance, uses of the method for evaluating a test substance according to the present invention and the like. It is therefore preferred to appropriately adjust the content of the test substance in the test solution in accordance with the kind of the test substance, uses of the method for evaluating a test substance according to the present invention and the like.

The dynamics of the whole sweat gland can be observed in the same manner as in the step (C) used in the method for observing dynamics of a sweat gland.

In the step (d), whether or not the test substance has a perspiration-controlling action is evaluated based on dynamics of the whole sweat gland observed in the step (c). The presence or absence of the perspiration-controlling action of the test substance can be evaluated based only on dynamics of the whole sweat gland which is contacted with the test substance. The presence or absence of the perspiration-controlling action of the test substance can be evaluated based on dynamics of the sweat gland which is contacted with the test substance and dynamics of the sweat gland which is not contacted with the test substance (the sweat gland not contacted with the test substance).

In the method for evaluating a test substance according to the present invention, it is preferred that dynamics of the whole sweat gland which is not contacted with the test substance and dynamics of the sweat gland which is contacted with the test substance are observed in the step (c) from the viewpoint of more accurate evaluation of whether or not the test substance has a perspiration-controlling effect. In this case, in the step (d), it is preferred that whether the test substance has a perspiration-controlling action is evaluated by comparing dynamics of the whole sweat gland which is not contacted with the test substance with dynamics of the whole sweat gland after contacting with the test substance.

When dynamics of the whole sweat gland which is not contacted with the test substance is observed, the following procedure 1 or 2 can be carried out in the step (c) and the step (d).

(Procedure 1)

In the step (c), one observation sample is used. Dynamics of the whole sweat gland contained in the observation sample is observed. Thereafter, the whole sweat gland contained in the observation sample is contacted with the test substance, and then dynamics of the resulting whole sweat gland is observed. In the step (d), whether or not test substance has a perspiration-controlling action can be evaluated based on a difference in dynamics of the whole sweat gland before and after contacting with the test substance.

Examples of a criterion for determining that the test substance has an antiperspirant action in the procedure 1 include that a change of dynamics of the whole sweat gland after contacting with the test substance with the passage of time is smaller than a change of dynamics of the whole sweat gland which is not contacted with the test substance, that is, dynamics of the sweat gland before contacting with the test substance with the passage of time, and the like. In addition, examples of a criterion for determining that the test substance has a perspiration-inducing action include that a change of dynamics of the whole sweat gland after contacting with the test substance with the passage of time is larger than changes of dynamics of the whole sweat gland which is not contacted with the test substance, that is, dynamics of the whole sweat gland before contacting with the test substance with the passage of time.

A stimulant can also be used from the viewpoint of more accurate evaluation in the case whether or not the test substance has an antiperspirant action is evaluated by carrying out the procedure 1. In this case, one observation sample is used in the step (c). The whole sweat gland contained in the observation sample is contacted with the stimulant, and then dynamics of the whole sweat gland is observed. Thereafter, the whole sweat gland contained in the observation sample is contacted with the test substance, and then dynamics of the whole sweat gland is observed. In the step (d), whether or not the test substance has a perspiration-controlling action can be evaluated by using a difference in dynamics of the whole sweat gland before and after contacting with the test substance.

(Procedure 2)

In the step (c), at least two kinds of observation samples are used, and the following steps are performed:

(c2-1) observing dynamics of the whole sweat gland contained in one kind of observation sample selected from the at least two kinds of observation samples when the whole sweat gland has not been contacted with the test substance, and (c2-2) contacting the whole sweat gland contained in an observation sample which is different from the observation sample used in the step (c2-1) with the test substance, and then observing dynamics of the whole sweat gland. In the step (d), whether or not the test substance has a perspiration-controlling action is evaluated based on a difference between dynamics of the sweat gland observed in the step (c2-1) and dynamics of the whole sweat gland observed in the step (c2-2).

Examples of a criterion for determining that the test substance has an antiperspirant action in the procedure 2 include that a change of dynamics of the whole sweat gland observed in the step (c2-2) with the passage of time is smaller than changes of dynamics of the whole sweat gland observed in (c2-1) with the passage of time. In addition, examples of a criterion for determining that the test substance has a perspiration-inducing action include that a change of dynamics of the whole sweat gland observed in the step (c2-2) with the passage of time is larger than changes of dynamics of the whole sweat gland observed in the step (c2-1) with the passage of time.

It is preferred that a stimulant is used in evaluation in which whether or not the test substance has an antiperspirant action is evaluated by carrying out the procedure 2 from the viewpoint of carrying out more accurate evaluation. In this case, there can be carried out as the step (c2-1), the step of contacting the whole sweat gland contained in one kind of observation sample selected from the group consisting of at least two kinds of the observation samples with the stimulant, to observe dynamics of the whole sweat gland not contacted with the test substance (in the case where the whole sweat gland has not been contacted with the test substance) (c2-1A). At least one of the following steps (c2-1A-1), (c2-1A-2) and (c2-1A-3) can be carried out as the step (c2-1) when a control substance is further used as a control for the test substance in addition to the stimulant.

Step (c2-1A-1)

The step includes a step of contacting the whole sweat gland contained in one kind of the observation sample selected from the group consisting of at least two kinds of the observation samples with a control substance, contacting the whole sweat gland with a stimulant, and thereafter observing dynamics of the whole sweat gland.

Step (c2-1A-2)

The step includes a step of contacting the whole sweat gland contained in one kind of the observation sample selected from the group consisting of at least two kinds of the observation samples with the stimulant, contacting the whole sweat gland with the control substance, and thereafter observing dynamics of the whole sweat gland.

Step (c2-1A-3)

The step includes a step of simultaneously contacting the whole sweat gland contained in one kind of the observation sample selected from the group consisting of at least two kinds of the observation samples, the control substance and the stimulant with one another, and thereafter observing dynamics of the whole sweat gland.

In addition, when the stimulant is used in evaluation in which whether or not the test substance has an antiperspirant action is evaluated by carrying out the procedure 2, there can be carried out as the step (c2-2), a step (c2-2A) including the step of contacting the whole sweat gland contained in an observation sample which is different from the observation sample used in (c2-1), the test substance and the stimulant with one another, and thereafter observing dynamics of the whole sweat gland. For example, at least one step of the following steps (c2-2-1), (c2-2-2) and (c2-2-3) can be carried out as the step (c2-2A).

Step (c2-2-1)

The step includes a step of contacting a whole sweat gland contained in an observation sample which is different from the observation sample used in the step (c 2-1) with the test substance, contacting the whole sweat gland with the stimulant, and thereafter observing dynamics of the whole sweat gland.

Step (c2-2-2)

The step includes a step of contacting a whole sweat gland contained in an observation sample which is different from the observation sample used in the step (c2-1) with the stimulant, contacting the whole sweat gland with the test substance, and thereafter observing dynamics of the whole sweat gland.

Step (c2-2-3)

The step includes a step of simultaneously contacting a whole sweat gland contained in an observation sample which is different from the observation sample used in the step (c2-1), the test substance and the stimulant with one another, and thereafter observing dynamics of the whole sweat gland.

The stimulant used in the method for evaluating a test substance according to the present invention is the same as the stimulant used in the method for observing dynamics of a sweat gland.

The amount of the stimulant to be contacted with the whole sweat gland and the contact duration cannot be absolutely determined because the amount of the stimulant to be contacted with the whole sweat gland and the contact duration vary depending on the kind of the stimulant and the like. Accordingly, it is preferred that the amount of the stimulant to be contacted with the whole sweat gland and the contact duration are appropriately determined in accordance with the kind of the stimulant and the like.

As explained above, since the method for evaluating a test substance according to the present invention can evaluate whether or not a test substance has a perspiration-controlling action, the method can be used for screening or evaluation of a perspiration-controlling component such as an antiperspirant component or a perspiration component. It is therefore expected that the method for evaluating a test substance according to the present invention is used for development of an external preparation such as a cosmetic.

EXAMPLES

Hereinafter, the present invention will be described in more detail with reference to working examples, but the present invention is not limited only to the working examples. In the following working examples and the like, the meanings of abbreviations are as follows:

Explanation of Abbreviations

BSA: bovine serum albumin
HEPES: 2-[4-(2-hydroxyethyl)piperazin-1-yl]ethane sulfonic acid
PBS: phosphate buffered saline
5×PBS: 5-fold concentration of phosphate buffered saline
10×PBS: 10-fold concentration of phosphate buffered saline Preparation Example 1

To 500 µL of phosphate-buffered physiological saline, 3.5 µL of a cytoskeleton-staining reagent (manufactured by Cytoskelton, trade name: Acti-stain 488, concentration of Acti-stain 488: 14 µM), 4 µL of a cell membrane-staining reagent (manufactured by Thermo Fisher Scientific, trade name: CellMask) and 1 µL of a nuclear staining reagent (Hoechst 33342) were added to obtain a staining reagent mixture.

Preparation Example 2

Seven-hundred microliters of collagen type I-A solution (content of collagen type I-A: 3% by mass) [manufactured by Nitta Gelatin Inc.] and 5 µL of 5×PBS [composition: 685 mM sodium chloride, 13.5 mM potassium chloride, 50 mM disodium hydrogenphosphate dodecahydrate and 9 mM potassium dihydrogenphosphate, pH 7.4] and 200 µL of a collagen reconstitution buffer [composition: 50 mM sodium hydroxide, 260 mM HEPES and 200 mM sodium bicarbonate, pH 10.0] were mixed to obtain a collagen-containing solution A. In addition, 800 µL of collagen type I-A solution (content of collagen type I-A: 3% by mass) [manufactured by Nitta Gelatin Inc.], 100 μL of 10×PBS [composition: 1370 mM sodium chloride, 27 mM potassium chloride, 100 mM disodium hydrogenphosphate dodecahydrate and 18 mM potassium dihydrogenphosphate, pH 7.4] and 100 μL of the collagen reconstitution buffer were mixed to obtain a collagen-containing liquid B.

Example 1

(1) Isolation of Whole Sweat Glands

As skin tissues, skin tissues which were refrigerated immediately after removal from living donors and stored at 4° C. for 15 hours were used. The skin tissues were immersed in a phosphate-buffered saline containing 10 μM Neutral Red, to incorporate Neutral Red into sweat glands included in the skin tissues. Next, the dermis of each of the skin tissues was finely cut to obtain dermal segments. Whole sweat glands were collected from the dermal segments by using tweezers under an optical microscope.

(2) Staining

The whole sweat glands obtained in Example 1(1) were immersed in the staining reagent mixture obtained in Preparation Example 1 at room temperature (24° C.) for 30 minutes, to stain the whole sweat glands. The stained whole sweat glands were washed with PBS.

(3) Positional Anchorage of Stained Whole Sweat Glands on the Support

The washed whole sweat glands obtained in Example 1(2) were allowed to stand on a glass bottom dish under a stereoscopic microscope (manufactured by Leica, trade name: M125). The collagen-containing liquid A obtained in Preparation Example 2 was added dropwise to the whole sweat glands that were allowed to stand on the glass bottom dish. Next, the glass bottom dish was incubated at 37° C. for 5 minutes to gelate the collagen type I-A contained in the collagen-containing liquid A placed on the whole sweat glands. Thereafter, an isotonic solution (PBS) was added onto the whole sweat glands to prevent the whole sweat glands from drying. Thus, the whole sweat glands were held on the glass bottom dish as a support with the collagen type I-A so that the position of each of the whole sweat glands was retained, to obtain an observation sample.

(4) Observation

While adhesion of the whole sweat glands to the glass bottom dish with the gelated collagen type I-A was confirmed under the stereoscopic microscope, 400 μL of Dulbecco's phosphate buffer [manufactured by Gibco, Catalog No. 14190-144] was added to the gelated collagen type I-A.

After 5 minutes passed from the addition of the buffer, the observation with the time-lapse imaging of the whole sweat glands on the glass bottom dish was started by using a confocal laser scanning microscope for biological use (inverted microscope (manufactured by Olympus Corporation, trade name: IX-83) equipped with FV 1200 manufactured by Olympus Corporation)). At that time, the whole sweat glands were visualized by detecting fluorescence derived from the nuclear staining reagent bound to the nucleus and fluorescence derived from the cytoskeleton-staining reagent bound to the cytoskeleton. After 60 seconds passed from the initiation of the observation, pilocarpine, which was a sweat gland contraction-inducing reagent (stimulant), was added to the whole sweat glands so as to have a concentration of 10 mM. The conditions of time-lapse imaging are as follows:

<Time-Lapse Imaging Conditions>
X: 126. 728 μm
y: 76. 136 μm
Z: 16 μm
Z interval: 2 μm
Number of Z slices: 9 slices
Time interval: 40 seconds
Total number of frames: 51 frames
Total observation duration: 30 minutes or more The results of dynamics of each of sweat glands obtained in Example 1 observed by time-lapse imaging based on fluorescence derived from the nuclear staining reagent and fluorescence derived from the cytoskeleton-staining reagent are shown in FIG. 2. The panels (A1) to (G1) in FIG. 2 are images of sweat glands double-stained with a nuclear staining reagent and a cytoskeleton-staining reagent. Panels (A2) to (G2) shown in FIG. 2 are images of sweat glands stained with a nuclear staining reagent corresponding to the panels (A1) to (G1), respectively. Panels (A3) to (G3) shown in FIG. 2 are images of sweat glands stained with a cytoskeleton-staining reagent corresponding to the panels (A1) to (G1), respectively. The correspondence relationship between the panels (A1) to (G3) shown in FIG. 2 and the elapsed time from the initiation of observation is shown in Table 1. In addition, the scale bar shown in FIG. 2 means 50 μm.

TABLE 1

| | | | Elapsed time from initiation of observation (sec.) |
|---|---|---|---|
| (A1) | (A2) | (A3) | 0 |
| (B1) | (B2) | (B3) | 160 |
| (C1) | (C2) | (C3) | 360 |
| (D1) | (D2) | (D3) | 560 |
| (E1) | (E2) | (E3) | 760 |
| (F1) | (F2) | (F3) | 960 |
| (G1) | (G2) | (G3) | 1160 |

In addition, the cells A, B, C and D (see FIG. 3) were selected from the image of FIG. 2, and then changes of a moving distance of each cell with the passage of time and changes of distance between cells with the passage of time were examined. First, the change (difference) in coordinates between consecutive frames was calculated by using X-coordinate and Y-coordinate of each cell in accordance with the formulae (I) and (II):

$$X_{n+1}-X_n \qquad (I)$$

wherein n represents an integer of 1 to 30, and $$Y_{n+1}-Y_n \qquad (II)$$

wherein n is the same as mentioned above. Next, in accordance with the Pythagorean theorem ($a^2+b^2=c^2$), the movement value between cells for each successive frame was obtained by calculating a square root of the formula (III):

$$(X_{n+1}-X_n)^2+(Y_{n+1}-Y_n)^2 \qquad (III)$$

wherein n is the same as mentioned above. Furthermore, in order to obtain an actual moving distance, the unit per coordinate 1 (μm/pixel) was obtained from the size of the obtained image [126.728×76.136 (unit: μm$^2$)] and the pixel (512×306). The actual moving distance (μm) of the cell was calculated by multiplying the movement value by the size per coordinate 1.

In Example 1, changes of the distance between two cells included in the sweat glands shown in FIG. 2 with the passage of time are shown in FIG. 4. In FIG. 4, (A) shows the distance between the cell A and the cell B, (B) shows the distance between the cell A and the cell C, (C) shows the distance between the cell A and the cell D, (D) shows the distance between the cell B and the cell C, (E) shows the distance between the cell B and the cell D, and (F) shows the distance between the cell C and the cell D.

In Example 1, changes of a moving distance of each cell included in the sweat glands shown in FIG. 2 with the passage of time are shown in FIG. 5. In FIG. 5, (A) shows the moving distance of the cell A, (B) shows the moving distance of the cell B, (C) shows the moving distance of the cell C, and (D) shows the moving distance of the cell D.

From the results shown in FIG. 4, it can be seen that the distance between the cell A and the cell B, the distance between the cell A and the cell C, the distance between the cell A and the cell D, the distance between the cell B and the cell C, the distance between the cell B and the cell D, and the distance between the cell C and the cell D change with the passage of time.

Further, from the results shown in FIG. 5, it can be seen that the moving distances of the cell A, the cell B, the cell C, and the cell D become larger when 150 to 300 seconds passed from the initiation of the observation, respectively.

Accordingly, from these results, it can be seen that dynamics of each of sweat glands in a living state can be observed by staining the isolated whole sweat glands in a living state with any of a cytoskeleton-staining reagent, a cell membrane-staining reagent and a nuclear staining reagent, and holding the whole sweat glands on a support with collagen type I so that the position of each of the whole sweat glands is retained.

Example 2

Dynamics of each of sweat glands was observed in the same manner as in Example 1 except for modifications shown in the following items (i), (ii), (iii) and (iv):

(i) The collagen-containing liquid B obtained in Preparation Example 2 was used in place of the collagen-containing liquid A.

(ii) Fluorescence derived from the nuclear staining reagent bound to the nucleus and fluorescence derived from the cell membrane-staining reagent bound to the cell membrane were detected in place of fluorescence derived from the nuclear staining reagent bound to the nucleus and fluorescence derived from the cytoskeleton-staining reagent bound to the cytoskeleton.

(iii) Acetylcholine which was a sweat gland contraction-inducing reagent was used in place of pilocarpine which was a sweat gland contraction-inducing agent.

(iv) A sweat gland contraction-inducing reagent was added to the whole sweat glands after 10 minutes passed from the initiation of the observation in place of the whole sweat glands after 60 seconds passed from the initiation of the observation.

Conditions for time-lapse imaging are as follows:
<Time-Lapse Imaging Conditions>
X: 116. 127 μm
y: 185. 679 μm
Z: 34. 6 μm
Z interval: 5 μm
Number of Z slices: 8 slices
Time interval: 30 seconds
Total number of frames: 66 frames
Total observation duration: 30 minutes or more The results of dynamics of each of sweat glands shown in Example 2 observed by time-lapse imaging based on fluorescence derived from the nuclear staining reagent and fluorescence derived from the cell membrane-staining reagent are shown in FIG. 6. Panels (A1) to (G1) shown in FIG. 6 are images of sweat glands double-stained with the nuclear staining reagent and the cell membrane-staining reagent. Panels (A2) to (G2) shown in FIG. 6 are images of sweat glands stained with the nuclear staining reagents corresponding to the panels (A1) to (G1), respectively. Panels (A3) to (G3) shown in FIG. 6 are images of sweat glands stained with the cell membrane-staining reagents corresponding to the panels (A1) to (G1), respectively. The correspondence relationship between the panels (A1) to (G3) shown in FIG. 6 and the elapsed time from the initiation of observation are shown in Table 2. In addition, the scale bar shown in FIG. 6 means 50 μm.

TABLE 2

| | | | Elapsed time from initiation of observation (sec.) |
|---|---|---|---|
| (A1) | (A2) | (A3) | 0 |
| (B1) | (B2) | (B3) | 120 |
| (C1) | (C2) | (C3) | 270 |
| (D1) | (D2) | (D3) | 420 |
| (E1) | (E2) | (E3) | 570 |
| (F1) | (F2) | (F3) | 720 |
| (G1) | (G2) | (G3) | 870 |

From the results shown in FIG. 6, it can be seen that the sweat glands move with the passage of time. From the above results, it can be seen that dynamics of each of sweat glands in a living state can be observed by staining the isolated whole sweat glands in a living state with any of a cytoskeleton-staining reagent, a cell membrane-staining reagent and a nuclear staining reagent, and holding the whole sweat glands on a support with collagen so that the position of each of the whole sweat glands is retained.

Example 3

(1) Isolation of Whole Sweat Glands
Whole sweat glands were isolated from the skin tissues in the same manner as in Example 1 (1).

(2) Staining
Staining was carried out in the same manner as in Example 1(2).

(3) Positional Anchorage of Stained Whole Sweat Glands on Support
The washed whole sweat glands obtained in Example 3(2) were allowed to stand on a glass bottom dish under a stereoscopic microscope (manufactured by Leica, trade name: M125). Next, PBS containing 3% by mass of a low melting point agarose kept at 40° C. was added dropwise to the whole sweat glands. The whole sweat glands after dropping the low melting point agarose were allowed to stand for 10 minutes at room temperature (24° C.) for 10 minutes, to gelate the low melting point agarose. Thereafter, the isotonic solution [extracellular solution (composition: 140 mM sodium chloride, 5 mM potassium chloride, 2 mM calcium chloride, 2 mM magnesium chloride, 10 mM HEPES buffer and 10 mM glucose, pH 7.4)] was added onto the gelated low melting agarose. Thus, the whole sweat glands were held on a glass bottom dish as a support with the low melting point agarose so that the position of each of the whole sweat glands was retained, to obtain an observation sample.

(4) Observation
Dynamics of each of sweat glands was observed in the same manner as in Example 1(4) except that in Example 1(4), the observation sample obtained in Example 3(3) was used in place of the observation sample obtained in Example 1(3); in Example 1(4), fluorescence derived from the nuclear staining reagent bound to the nucleus was detected in place of fluorescence derived from the nuclear staining reagent bound to the nucleus and fluorescence derived from the cytoskeleton-staining reagent bound to the cytoskeleton; in Example 1(4), a sweat gland contraction-inducing reagent was added to the whole sweat glands after 10 minutes passed from the initiation of the observation in place of the whole sweat glands after 60 seconds passed from the initiation of the observation. Conditions for time-lapse imaging are as follows:

<Time-Lapse Imaging Conditions>
X: 319. 194 µm
y: 227.286 µm
Z: 30.0 µm
Z interval: 2 µm
Number of Z slices: 16 slices
Time interval: 10 seconds
Total number of frames: 201 frames
Total observation duration: 30 minutes or more The results of dynamics of each of sweat glands obtained in Example 3 observed by time-lapse imaging based on fluorescence derived from the nuclear staining reagent are shown in FIG. 7. Panels (A1) to (G1) shown in FIG. 7 are images of sweat glands stained with the nuclear staining reagent. The correspondence relationship between the panels (A1) to (G1) described in FIG. 7 and the elapsed time from the initiation of observation are shown in Table 3. In addition, the scale bar shown in FIG. 7 means 100 µm.

TABLE 3

|  | Elapsed time passed from initiation of observation (sec.) |
|---|---|
| (A1) | 0 |
| (B1) | 200 |
| (C1) | 400 |
| (D1) | 600 |
| (E1) | 800 |
| (F1) | 1000 |
| (G1) | 1200 |

In addition, the cells indicated by the arrows shown in FIG. 7 were selected, and thereafter changes of a moving distance of one of the cell were examined with the passage of time.

In Example 3, changes of a moving distance of each cell included in sweat glands with the passage of time, which were obtained from the adjacent panels of FIG. 7 are shown in FIG. 8.

From the results shown in FIG. 8, it can be seen that a cell movement is observed with the passage of time. From the above results, it can be seen that dynamics of each of sweat glands in a living state can be observed by staining the isolated whole sweat glands in a living state using any of a cytoskeleton-staining reagent, a cell membrane-staining reagent and a nuclear staining reagent, and holding the whole sweat glands on a support with agarose so that the position of each of the whole sweat glands is retained.

Example 4

(1) Isolation of Whole Sweat Glands
The whole sweat glands were isolated from the skin tissues in the same manner as in Example 1(1).

(2) Staining
Staining was carried out in the same manner as in Example 1(2).

(3) Positional anchorage of stained whole sweat glands on support
An observation sample was obtained in the same manner as in Example 1(3) excepted that basement membrane matrix (manufactured by Corning, trade name: Matrigel® Growth Factor Reduced (GFR) Basement Membrane Matrix) was used in place of the collagen type I-A in Example 1(3).

(4) Observation
Dynamics of each of sweat glands was observed in the same manner as in Example 1(4) except that in Example 1(4), the observation sample obtained in Example 4(3) was used in place of the observation sample obtained in Example 1(3); in Example 1(4), fluorescence derived from the nuclear staining reagent bound to the nucleus was detected in place of fluorescence derived from the nuclear staining reagent bound to the nucleus and fluorescence derived from the cytoskeleton-staining reagent bound to the cytoskeleton; in Example 1(4), a sweat gland contraction-inducing reagent was added to the whole sweat glands after 10 minutes passed from the initiation of the observation in place of the whole sweat glands after 60 seconds passed from the initiation of the observation. Conditions for time-lapse imaging are as follows:

<Time-Lapse Imaging Conditions>
X: 274. 482 µm
y: 401. 166 µm
Z: 44. 0 µm
Z interval: 2 µm
Number of Z slices: 23 slices
Time interval: 20 seconds
Total number of frames: 101 frames
Total observation duration: 30 minutes or more The results of dynamics of each of sweat glands obtained in Example 4 observed by time-lapse imaging based on fluorescence derived from the nuclear staining reagent are shown in FIG. 9. Panels (A1) to (G1) shown in FIG. 9 are images of sweat glands stained with the nuclear staining reagent. The correspondence relationship between the panels (A1) to (G1) shown in FIG. 9 and the elapsed time from the initiation of observation is the same as that between the panel (A1) to (G1) and the elapsed time from the initiation of observation shown in Table 3. In addition, the scale bar shown in FIG. 9 means 200 µm.

In addition, cells indicated by the arrows shown in FIG. 9 were selected, and thereafter changes of a moving distance of a cell were examined with the passage of time.

In Example 4, changes of a moving distance of each cell included in sweat glands with the passage of time, which were obtained from the adjacent panels of FIG. 9 are shown in FIG. 10.

From the results shown in FIG. 10, it can be seen that a movement of a cell is observed with the passage of time. From the above results, it can be seen that dynamics of each of sweat glands in a living state can be observed by staining the isolated whole sweat glands in a living state with any of a cytoskeleton-staining reagent, a cell membrane-staining reagent and a nuclear staining reagent, and holding the whole sweat gland on a support with basement membrane matrix so that the position of each of the whole sweat glands is retained.

Example 5

(1) Isolation of Whole Sweat Glands

Whole sweat glands were isolated from the skin tissues in the same manner as in Example 1(1).

(2) Staining

Staining was carried out in the same manner as in Example 1(2).

(3) Positional Anchorage of Stained Whole Sweat Glands on Support

An aqueous solution containing 200 μg/mL poly-D-lysine was applied onto the surface of the glass bottom dish. The glass bottom dish applied was incubated at 37° C. for 2 hours. The glass bottom dish after the incubation was washed twice with a sterilized water. Thus, a poly-lysine-coated glass bottom dish was obtained.

Next, the washed whole sweat glands, which was obtained in Example 1(2) was allowed to stand on a poly-lysine-coated glass bottom dish under a stereoscopic microscope (manufactured by Leica, trade name: M125). Thereafter, an isotonic solution (extracellular solution) was added onto the whole sweat glands to prevent the whole sweat glands from drying. Thus, the whole sweat glands were held on the glass bottom dish as a support with poly-D-lysine so that the position of each of the whole sweat glands was retained, to obtain an observation sample.

(4) Observation

Dynamics of each of sweat glands was observed in the same manner as in Example 1(4) except that in Example 1(4), the observation sample obtained in Example 5(3) was used in place of the observation sample obtained in Example 1(3); in Example 1(4), fluorescence derived from the nuclear staining reagent bound to the nucleus was detected in place of fluorescence derived from the nuclear staining reagent bound to the nucleus and fluorescence derived from the cytoskeleton-staining reagent bound to the cytoskeleton; in Example 1(4), a sweat gland contraction-inducing reagent was added to the whole sweat glands after 10 minutes passed from the initiation of the observation in place of the whole sweat glands after 60 seconds passed from the initiation of the observation. Conditions for time-lapse imaging are as follows:

<Time-Lapse Imaging Conditions>
X: 403.65 μm
y: 271. 988 μm
Z: 70 μm
Z interval: 2 μm
Number of Z slices: 36 slices
Time interval: 20 seconds
Total number of frames: 101 frames
Total observation duration: 30 minutes or more In Example 5, the results of dynamics of each of sweat glands observed by time-lapse imaging based on fluorescence derived from nuclear staining reagent are shown in FIG. 11. Panels (A1) to (G1) shown in FIG. 11 are images of sweat glands stained with a nuclear staining reagent. The correspondence relationship between the panels (A1) to (G1) shown in FIG. 11 and the elapsed time from the initiation of observation is the same as that between the panel (A1) to (G1) and the elapsed time from the initiation of observation shown in Table 3. In addition, the scale bar shown in FIG. 11 means 200 μm.

In addition, the cells indicated by the arrows shown in FIG. 11 were selected, and thereafter changes of a moving distance of a cell were examined with the passage of time.

In Example 5, changes of a moving distance of each cell included in the sweat glands with the passage of time, which were obtained from the adjacent panels of FIG. 11 are shown in FIG. 12.

From the results shown in FIG. 12, it can be seen that a cell movement is observed with the passage of time. From these results, it can be seen that dynamics of each of sweat glands in a living state can be observed by staining the isolated whole sweat glands in a living state with any of a cytoskeleton-staining reagent, a cell membrane-staining reagent and a nuclear staining reagent, and holding the whole sweat glands on the support with poly-D-lysine so that the position of each of the whole sweat glands is retained.

Example 6

(1) Isolation of Whole Sweat Glands

Whole sweat glands were isolated from the skin tissues in the same manner as in Example 1(1).

(2) Staining

Staining was carried out in the same manner as in Example 1(2).

(3) Positional Anchorage of Stained Whole Sweat Glands on Support

An aqueous solution containing 200 μg/mL poly-D-lysine was applied onto the surface of a glass bottom dish. The glass bottom dish applied was incubated at 37° C. for 30 min. The glass bottom dish after the incubation was washed twice with a sterilized water. Thus, a poly-lysine-coated glass bottom dish was obtained.

Next, an aqueous solution containing 20 μg/mL laminin was applied onto the surface of the poly-lysine-coated glass bottom dish. The coated glass bottom dish was incubated at 37° C. for 2 hours. The glass bottom dish after the incubation was washed twice with a sterilized water. Thus, a poly-lysine-laminin-coated glass bottom dish was obtained.

Thereafter, the washed whole sweat glands obtained in Example 1(2) were allowed to stand on the poly-lysine-laminin-coated glass bottom dish under a stereoscopic microscope (manufactured by Leica, trade name: M125). After that, an isotonic solution (extracellular solution) was added onto the whole sweat glands to prevent the whole sweat glands from drying. Thus, the whole sweat glands were held on the glass bottom dish as a support with poly-D-lysine and laminin in combination so that the position of each of the whole sweat glands was retained, to obtain an observation sample.

(4) Observation

Dynamics of each of sweat glands was observed in the same manner as in Example 1(4) except that in Example 1(4), the observation sample obtained in Example 6(3) was used in place of the observation sample obtained in Example 1(3); in Example 1(4), fluorescence derived from the nuclear staining reagent bound to the nucleus was detected in place of fluorescence derived from the nuclear staining reagent bound to the nucleus and fluorescence derived from the cytoskeleton-staining reagent bound to the cytoskeleton; in Example 1(4) a sweat gland contraction-inducing reagent was added to the whole sweat glands after 10 minutes passed from the initiation of the observation in place of the whole sweat glands after 60 seconds passed from the initiation of the observation. Conditions for time-lapse imaging are as follows:

<Time-Lapse Imaging Conditions>
X: 351. 486 μm
y: 614. 79 μm

Z: 34. 0 μm
Z interval: 2 μm
Number of Z slices: 18 slices
Time interval: 20 seconds
Total number of frames: 101 frames
Total observation duration: 30 minutes or more The results of dynamics of each of sweat glands obtained in Example 6 observed by time-lapse imaging based on fluorescence derived from the nuclear staining reagent are shown in FIG. 13. Panels (A1) to (G1) shown in FIG. 13 are images of sweat glands stained with a nuclear staining reagent. The correspondence relationship between the panels (A1) to (G1) shown in FIG. 13 and the elapsed time from the initiation of observation is the same as that between the panel (A1) to (G1) and the elapsed time from the initiation of observation shown in Table 3. In addition, the scale bar shown in FIG. 13 means 200 μm.

In addition, the cells indicated by the arrows shown in FIG. 13 were selected, and thereafter changes of a moving distance of each cell were examined with the passage of time.

In Example 6, changes of a moving distance of each cell included in sweat glands with the passage of time, which were obtained from the adjacent panels of FIG. 13 are shown in FIG. 14.

From the results shown in FIG. 14, it can be seen that a cell movement is observed with the passage of time. From these results, it can be seen that dynamics of each of sweat glands in a living state can be observed by staining the isolated whole sweat glands in a living state with any of a cytoskeleton-staining reagent, a cell membrane-staining reagent and a nuclear staining reagent, and holding the whole sweat glands on the support with poly-D-lysine and laminin in combination so that the position of each of the whole sweat glands is retained.

Example 7

(1) Isolation of Whole Sweat Gland

Whole sweat glands were isolated from the skin tissues in the same manner as in Example 1(1).

(2) Staining

Staining was carried out in the same manner as in Example 1(2).

(3) Positional Anchorage of Stained Whole Sweat Glands on Support

A membrane was obtained by cutting out a membrane part from a product under the trade name of Millicell Cell Culture Insert manufactured by Merck Millipore.

Next, the washed whole sweat glands obtained in Example 1(2) were allowed to stand on a glass bottom dish under a stereoscopic microscope (manufactured by Leica, trade name M125). The membrane was placed on the whole sweat glands which were allowed to stand on the glass bottom dish. Thereafter, an isotonic solution (extracellular solution) was added onto the whole sweat glands to prevent the whole sweat glands from drying. Thus, the whole sweat glands were held on the glass bottom dish as a support with the membrane so that the position of each of the whole sweat glands was retained, to obtain an observation sample.

(4) Observation

Dynamics of each of sweat glands was observed in the same manner as in Example 1(4) except that in Example 1(4), the observation sample obtained in Example 7(3) was used in place of the observation sample obtained in Example 1(3); in Example 1(4), fluorescence derived from the nuclear staining reagent bound to the nucleus was detected in place of fluorescence derived from the nuclear staining reagent bound to the nucleus and fluorescence derived from the cytoskeleton-staining reagent bound to the cytoskeleton; a sweat gland contraction-inducing reagent was added to the whole sweat glands after 10 minutes passed from the initiation of the observation in place of the whole sweat glands after 60 seconds passed from the initiation of the observation. Conditions for time-lapse imaging are as follows:

<Time-Lapse Imaging Conditions>
X: 473.202 μm
y: 515. 43 μm
Z: 30 μm
Z interval: 2 μm
Number of Z slices: 16 slices
Time interval: 20 seconds
Total number of frames: 101 frames
Total observation duration: 30 minutes or more The results of dynamics of each of sweat glands obtained in Example 7 observed by time-lapse imaging based on fluorescence derived from the nuclear staining reagent are shown in FIG. 15. Panels (A1) to (G1) shown in FIG. 15 are stained images obtained by using the nuclear staining reagent. The correspondence relationship between the panels (A1) to (G1) shown in FIG. 15 and the elapsed time from the initiation of observation is the same as that between the panel (A1) to (G1) and the elapsed time from the initiation of observation shown in Table 3. In addition, the scale bar shown in FIG. 15 means 200 μm.

In addition, the cells indicated by the arrows shown in FIG. 15 were selected for examining changes of a moving distance of each cell with the passage of time.

In Example 7, changes of a moving distance of each cell included in sweat glands with the passage of time, which were obtained from the adjacent panels of FIG. 15 are shown in FIG. 16.

From the results shown in FIG. 16, it can be seen that a cell movement is observed with the passage of time. From these results, it can be seen that dynamics of each of sweat glands in a living state can be observed by staining the isolated whole sweat glands in a living state with any of a cytoskeleton-staining reagent, a cell membrane-staining reagent and a nuclear staining reagent, and holding the whole sweat glands on a support with a membrane so that the position of each of the whole sweat glands is retained.

Comparative Example 1

(1) Isolation of Whole Sweat Gland

Whole sweat glands were isolated from the skin tissues in the same manner as in Example 1(1).

(2) Staining

Staining was carried out in the same manner as in Example 1(2).

(3) Positional Anchorage of Stained Whole Sweat Glands on Support

An aqueous solution containing 20 μg/mL laminin was applied onto the surface of a glass bottom dish. The glass bottom dish applied was incubated at 37° C. for 2 hours. The glass bottom dish after the incubation was washed twice with a sterilized water. Thus, a laminin-coated glass bottom dish was obtained.

Thereafter, the washed whole sweat glands obtained in Example 1(2) was allowed to stand on the laminin-coated glass bottom dish under a stereoscopic microscope (manufactured by Leica, trade name: M125). Thereafter, an isotonic solution (extracellular solution) was added onto the whole sweat glands to prevent the whole sweat glands from drying, to obtain an observation sample.

(4) Observation

Dynamics of each of sweat glands was observed in the same manner as in Example 1(4) except that in Example 1(4), the observation sample obtained in Comparative Example 1(3) was used in place of the observation sample obtained in Example 1(3); in Example 1(4), fluorescence derived from the nuclear staining reagent bound to the nucleus was detected in place of fluorescence derived from the nuclear staining reagent bound to the nucleus and fluorescence derived from the cytoskeleton-staining reagent bound to the cytoskeleton; in Example 1(4), a sweat gland contraction-inducing reagent was added to the whole sweat glands after 10 minutes passed from the initiation of the observation in place of the whole sweat glands after 60 seconds passed from the initiation of the observation.

As a result, since the sweat glands were shifted in position, dynamics of each of the sweat glands could not be observed.

As described above, it can be seen that dynamics of each of sweat glands in a living state can be observed by using the observation sample which was obtained by staining the isolated whole sweat glands in a living state with any of a cytoskeleton-staining reagent, a cell membrane-staining reagent and a nuclear staining reagent, and holding the whole sweat glands on the support with at least one material selected from the group consisting of collagen, agarose, basement membrane matrix, poly-D-lysine and a membrane so that the position of each of the whole sweat glands is retained.

Example 8

Whole sweat glands were observed by time-lapse imaging in the same manner as in Example 1 except that Krebs-Ringer solution (composition: 125 mM sodium chloride, 5 mM potassium chloride, 1 mM calcium chloride, 1.2 mM magnesium chloride, 25 mM sodium bicarbonate, 1.2 mM dihydrogen phosphate sodium, 5 mM glucose and 10 mg/100 mL of fatty acid-free bovine serum albumin, pH 7.48) was used in place of PBS. After 10 minutes passed from the initiation of the observation, pilocarpine which was a sweat gland contraction-inducing reagent (stimulant) was added to the whole sweat glands so as to have a concentration of 10 mM, and thereafter the observation of the whole sweat glands using the time-lapse imaging was continued.

Next, changes of each outer diameter index values at the determined sites (A) to (C) shown in FIG. 17 with the passage of time were obtained by using the image analysis software (manufactured by BITPLANE, trade name: Imaris). The outer diameter index value was obtained by stacking data in the Z direction and performing calculation in which the image analysis software was used in the "Surface" mode under the following setting conditions:

<Setting Conditions for Determined Site (A)>
Manual Threshold Value=650.963,
Manual Threshold Value B=1539.68, and
Number of Voxels above 2.37e4.
<Setting Conditions for Determined Site (B)>
Manual Threshold Value=588.389,
Manual Threshold Value B=1629.69, and
Number of Voxels above 2.84e4.
<Setting Conditions for Determined Site (C)>
Manual Threshold Value=353.494,
Manual Threshold Value B=1720.12, and
Number of Voxels above 2.69e4.

In FIG. 17, the determined site (A) is a portion enveloped by myoepithelial cells. The determined site (B) and the determined site (C) are portions which are not enveloped by myoepithelial cells, and which are flow pathways for sweat. Further, the scale bar in FIG. 17 means 50 μm.

After cancelling the stacking of the data in the Z direction, changes of an inner diameter index value at the determined sites (A) to (C) shown in FIG. 18 were calculated with one kind of data in the Z direction. The internal diameter index value was obtained by preparing the surface model, then extracting the components included in the surface model with Mask tool included in an image analysis software and performing calculation with the image analysis software under the following setting conditions:

<Setting Conditions for Determined Site (A)>
Manual Threshold Value=159.839,
Manual Threshold Value B=289.434, and
Distance to Image Border XY Between 40.6 μm and 2450 μm.
<Setting Conditions for Determined Site (B)>
Manual Threshold Value=305.011,
Manual Threshold Value B=585.989, and
Number of Voxels between 1.00 and 1091
Distance to Image Border XY Between 43.0 μm and 55.1 μm.
<Setting Conditions for Determined Site (C)>
Manual Threshold Value=365.977,
Manual Threshold Value B=518.235,
Number of Voxels between 1.00 and 1021,
Distance to Image Border XY Between 53.6 μm and 72.8 μm, and
Distance from Origin between 166 μm and automatic threshold.

Determined sites (A) to (C) shown in FIG. 18 correspond to determined sites (A) to (C) shown in FIG. 17. In FIG. 18, the scale bar means 50 μm.

In Example 8, changes over time in each outer diameter index value at the determined sites shown in the drawing-substituted photograph of FIG. 17 are shown in FIG. 19. In FIG. 19, (A) shows changes of the outer diameter index value at the determined site of (A) in FIG. 17 with the passage of time, (B) shows changes of the outer diameter index value at the determined site of (B) in FIG. 17 with the passage of time, and (C) shows changes of the outer diameter index value at the determined site (C) in FIG. 17 with the passage of time. In addition, in Example 8, changes of inner diameter index values at the determined sites shown in the drawing-substituted photograph of FIG. 18 with the passage of time are shown in FIG. 20. In FIG. 20, (A) shows changes of the inner diameter index value at the determined site (A) in FIG. 18 with the passage of time, (B) shows changes of the inner diameter index value at the determined site (B) with the passage of time, (C) shows changes in the inner diameter index value at the determined site (C) in FIG. 18 with the passage of time.

From the results shown in FIG. 19, it can be seen that the determined site (A) contracts after stimulating with the stimulant, and thereafter expands, since the outer diameter index value at the determined site (A) decreases after stimulating with the stimulant and then increases. In addition, it can be seen that the determined site (B) expands after stimulating with the stimulant, since the outer diameter index value at the determined site (B) increases after stimulating with the stimulant. Furthermore, it can be seen that the outer diameter index value at the determined site (C) hardly changes after stimulating with the stimulant.

From the results shown in FIG. 20, it can be seen that the determined site (A) contracts after stimulating with the stimulant, and thereafter expands, since the inner diameter index value at the determined site (A) greatly decreases after stimulating with the stimulant and then increases. In addition, it can be seen that the determined site (B) expands after passing the time from the termination of the stimulation with the stimulant, since the outer diameter index value at the determined site (B) hardly changes immediately after stimulating with the stimulant, but the outer diameter index value increases when passing a certain time. Further, it can be seen that the determined site (C) expands after passing the time from the termination of the stimulation with the stimulant, since the outer diameter index value at the determined site (C) hardly changes immediately after stimulating with the stimulant, but the outer diameter index value increases when passing a certain time.

From these results, it is suggested that a secretory portion of the sweat glands, which is enveloped with myoepithelial cells contracts, and an excretory portion of the sweat glands, which is not enveloped with myoepithelial cells expands, so that tubule of each of the sweat glands transports sweat to a sweat pathway.

Contraction and expansion of the sweat glands when PBS or an extracellular solution was used in place of Krebs-Ringer solution was examined. As a result, it was shown that the degree of contraction and expansion of the sweat glands when PBS or an extracellular solution was used was smaller than the degree of contraction and expansion of the sweat glands when Krebs-Ringer's solution was used.

As described above, it can be seen that movement of contraction and expansion can be well-observed by adding Krebs-Ringer's solution as a buffer onto whole sweat glands obtained by staining the isolated whole sweat glands in a living state with any of a cytoskeleton-staining reagent, a cell membrane-staining reagent and a nuclear staining reagent, and holding the whole sweat glands on a support with at least one material selected from the group consisting of collagen, agarose, basement membrane matrix, poly-D-lysine and a membrane.

Example 9

Whole sweat glands were observed by time-lapse imaging in the same manner as in Example 1 except that Krebs-Ringer solution was used in place of PBS, that atropine as a test substance was added onto the whole sweat glands before observing the whole sweat glands by using time-lapse imaging and thereafter the whole sweat glands were incubated for 30 minutes, and that pilocarpine was added onto the whole sweat glands so as to have a concentration of 10 mM after 10 minutes passed from the initiation of the observation (Experiment No. 1). Next, cells E, F, G, H and I were selected from the image of FIG. 21, and a moving distance of each cell was examined in the same manner as in Example 1. Next, the average value of moving distances of cells was obtained by using the moving distance of each cell. The scale bar in FIG. 21 means 50 μm.

In addition, whole sweat glands were observed by time-lapse imaging in the same manner as in Example 1 except that Krebs-Ringer's solution was used in place of PBS and that pilocarpine was added onto the whole sweat glands so as to have a concentration of 10 mM after 10 minutes passed from the initiation of the observation (Experiment No. 2). Next, cells J, K, L, M and N were selected from the image of FIG. 22, and a moving distance of each cell was examined in the same manner as in Example 1. Next, the average value of moving distances of cells was obtained by using the moving distance of each cell. The scale bar in FIG. 22 means 50 μm.

In Example 9, changes of a moving distance of each cell included in the sweat glands of Experiment number 1 with the passage of time are shown in FIG. 23. Changes of a moving distance of each cell included in the sweat glands of Experiment number 2 with the passage of time are shown in FIG. 24.

From the results shown in FIGS. 23 and 24, it can be seen that the changes of a moving distance of each cell included in the sweat glands contacted with atropine (FIG. 23) of Experiment number 1 with the passage of time are smaller than the changes of a moving distance of each cell included in the whole sweat glands not contacted with atropine (FIG. 24) of Experiment number 2 with the passage of time. From these results, it can be judged that atropine has an antiperspirant action. It can therefore be seen that whether or not the test substance has a perspiration-controlling action such as an antiperspirant action or the like is evaluated by using the observation sample obtained by staining the isolated sweat glands in a living state with a staining reagent, and holding the whole sweat glands on a support so that the position of each of the whole sweat glands is retained by using at least one material selected from the group consisting of collagen, agarose, basement membrane matrix, poly-D-lysine and a membrane.

DESCRIPTION OF SYMBOLS

1: sweat gland
2: secretory portion
3: excretory portion
4: skin
5: dermis
6: coil structure

The invention claimed is:

1. A method for observing dynamics of a sweat gland, comprising the steps of:
   (A) staining, without performing tissue fixation, an isolated whole sweat gland in a living state with at least one staining reagent selected from the group consisting of a staining reagent for a cell membrane, a staining reagent for a nucleus and a staining reagent for a cytoskeletal component,
   (B) holding the whole sweat gland stained in the step (A) on a support with at least one material selected from the group consisting of collagen, agarose, basement membrane matrix, poly-D-lysine and a membrane so that the position of the whole sweat gland stained in the step (A) is retained, to obtain an observation sample, and
   (C) observing dynamics of the whole sweat gland retained in the observation sample obtained in the step (B).

2. The method for observing dynamics of a sweat gland according to claim 1, wherein the step (B) further comprises the step of adding a buffer onto the whole sweat gland held on the support.

3. The method for observing dynamics of a sweat gland according to claim 2, wherein the buffer is a buffer containing 100 to 150 mM sodium chloride, 3 to 7 mM potassium chloride, 0.5 to 2 mM calcium chloride, 0.5 to 2 mM magnesium chloride, 20 to 30 mM sodium bicarbonate, 0.5 to 2 mM sodium dihydrogen phosphate, 2 to 8 mM glucose and 5 to 15 mg/100 mL of fatty acid-free bovine serum albumin, and having a pH of 7.1 to 7.6.

4. The method for observing dynamics of a sweat gland according to claim 1, wherein the step (C) further comprises the steps of contacting the whole sweat gland retained in the observation sample with a stimulant, and observing dynamics of the whole sweat gland caused by the stimulant.

5. A method for evaluating a test substance, wherein whether or not the test substance has perspiration-controlling action is evaluated, the method comprising the steps of:
(a) staining, without performing tissue fixation, an isolated whole sweat gland in a living state with at least one staining reagent selected from the group consisting of a staining reagent for a cell membrane, a staining reagent for a nucleus and a staining reagent for a cytoskeletal component,
(b) holding the whole sweat gland stained in the step (a) on a support with at least one material selected from the group consisting of collagen, agarose, basement membrane matrix, poly-D-lysine and a membrane so that the position of the whole sweat gland stained in the step (a) is retained, to obtain an observation sample,
(c) contacting the whole sweat gland retained in the observation sample with the test substance to observe dynamics of the whole sweat gland, and
(d) evaluating whether or not the test substance has a perspiration-controlling action based on dynamics of the whole sweat gland observed in the step (c).

6. The method for evaluating a test substance according to claim 5, wherein the step (b) further comprises the step of adding a buffer onto the whole sweat gland held on the support.

7. The method for evaluating a test substance according to claim 6, wherein the buffer is a buffer containing 100 to 150 mM sodium chloride, 3 to 7 mM potassium chloride, 0.5 to 2 mM calcium chloride, 0.5 to 2 mM magnesium chloride, 20 to 30 mM sodium bicarbonate, 0.5 to 2 mM sodium dihydrogen phosphate, 2 to 8 mM glucose and 5 to 15 mg/100 mL of fatty acid-free bovine serum albumin, and having a pH of 7.1 to 7.6.

8. The method for evaluating a test substance according to claim 5, wherein the step (c) further comprises the steps of contacting the whole sweat gland retained in the observation sample with the test substance and a stimulant, and observing the dynamics of the whole sweat gland.

9. The method for observing dynamics of a sweat gland according to claim 1, wherein the dynamics of the whole sweat gland in the step (C) is movement in contraction of a sweat gland.

10. The method for evaluating a test substance according to claim 5, wherein the dynamics of the whole sweat gland in the step (c) is movement in contraction of a sweat gland.

* * * * *